(12) United States Patent
Geddes

(10) Patent No.: US 8,759,110 B2
(45) Date of Patent: Jun. 24, 2014

(54) METAL ENHANCED FLUORESCENCE-BASED SENSING METHODS

(75) Inventor: Chris D. Geddes, Bel-Air, MD (US)

(73) Assignee: University of Maryland, Baltimore County, Baltimore, MD (US)

(*) Notice: Subject to any disclaimer, the term of this patent is extended or adjusted under 35 U.S.C. 154(b) by 44 days.

(21) Appl. No.: 13/104,146

(22) Filed: May 10, 2011

(65) Prior Publication Data

US 2011/0294997 A1 Dec. 1, 2011
US 2013/0102770 A9 Apr. 25, 2013

Related U.S. Application Data

(63) Continuation of application No. 11/917,804, filed as application No. PCT/US2006/023738 on Jun. 19, 2006, now Pat. No. 7,939,333, application No. 13/104,146, which is a continuation-in-part of application No. 10/536,502, filed as application No. PCT/US03/38163 on Nov. 26, 2003, now Pat. No. 8,114,598.

(60) Provisional application No. 60/691,851, filed on Jun. 17, 2005, provisional application No. 60/781,933, filed on Mar. 13, 2006, provisional application No. 60/429,263, filed on Nov. 26, 2002.

(51) Int. Cl.
*G01N 21/64* (2006.01)
*G01N 33/52* (2006.01)
*C07H 21/02* (2006.01)

(52) U.S. Cl.
USPC .......................................... 436/94; 436/164

(58) Field of Classification Search
USPC ........... 436/94, 164, 174; 435/6.1, 6.11, 6.16, 435/6.17, 6.18, 6.19
See application file for complete search history.

(56) References Cited

U.S. PATENT DOCUMENTS

| | | | |
|---|---|---|---|
| 4,069,016 A | 1/1978 | Wu | |
| 5,017,009 A | 5/1991 | Schutt et al. | |
| 5,449,918 A | 9/1995 | Krull et al. | |
| 5,866,433 A | 2/1999 | Schalkhammer et al. | |
| 7,253,452 B2 | 8/2007 | Steckel et al. | |
| 7,348,182 B2 | 3/2008 | Martin et al. | |

(Continued)

FOREIGN PATENT DOCUMENTS

| | | |
|---|---|---|
| GB | 1536425 A | 12/1978 |
| WO | WO 89/09408 | 10/1989 |

(Continued)

OTHER PUBLICATIONS

Aslan, Kadir et al. "Metal-enhanced fluorescence-based RNA sensing." JACS (2006) 128 4206-4207, s1-s9.*

(Continued)

*Primary Examiner* — Christopher A Hixson
(74) *Attorney, Agent, or Firm* — Marianne Fuierer; Moore & Van Allen, PLLC

(57) ABSTRACT

The present invention relates to metallic-surface detection systems for determining target substances including free bilirubin in neonatal serum in the presence of a predominantly high background of bilirubin bound Human Serum Albumin (HSA) or sensing and isolating target nucleotide sequences wherein a fluorescence signal is enhanced by close proximity of the target substances near metallic surfaces.

7 Claims, 17 Drawing Sheets

(56) References Cited

U.S. PATENT DOCUMENTS

| | | | |
|---|---|---|---|
| 7,351,590 | B2 | 4/2008 | Martin |
| 7,718,445 | B2 | 5/2010 | Martin |
| 2002/0045190 | A1* | 4/2002 | Wilson et al. ............... 435/7.1 |
| 2003/0059820 | A1* | 3/2003 | Vo-Dinh ....................... 435/6 |
| 2003/0228682 | A1 | 12/2003 | Lakowicz et al. |
| 2004/0106166 | A1 | 6/2004 | Matsumoto |
| 2004/0160606 | A1 | 8/2004 | Lakowicz et al. |
| 2006/0147927 | A1 | 7/2006 | Geddes et al. |
| 2007/0269826 | A1 | 11/2007 | Geddes |
| 2008/0096281 | A1 | 4/2008 | Geddes et al. |
| 2009/0022766 | A1 | 1/2009 | Geddes |
| 2011/0053788 | A1* | 3/2011 | Bamdad et al. ............... 506/9 |

FOREIGN PATENT DOCUMENTS

| | | |
|---|---|---|
| WO | WO 2004/024191 | 3/2004 |
| WO | WO 2004/059279 | 7/2004 |
| WO | WO 2004/059279 A2 | 7/2004 |
| WO | WO 2006/074130 | 7/2006 |
| WO | WO 2006/137945 | 12/2006 |

OTHER PUBLICATIONS

Lakowicz, J. R. (2001). Radiative Decay Engineering: Biophysical and Biomedical Applications, *Anal. BioChem.*, 298, 1-24.

Ghosh, Sujit Kumar et al. "Fluorescence quenching of 1-methylaminopyrene near gold nanoparticles: size regime dependence of the small metallic particles." Chemical Physical Letters (2004) 395 366-372.

Geddes, C. D. And Lakowicz, J. R. (2002). Metal-Enhanced Fluorescence, *J. Fluorescence*, 12:(2), 121-129.

Lakowicz, J. R., Shen, Y., D'Auria, S., Malicka, J., Fang, J., Gryczynski, Z. and Gryczynski, I. (2002). Radiative Decay Engineering 2. Effects of silver island films on fluorescence intensity Lifetimes and Resonance energy transfer, *Anal. Biochem.*, 301, 261-277.

Lakowicz, J. R., Gryczynski, I, Shen, Y. B., Malicka, J., and Gryczynski, Z, (2001). Intensified fluorescence, *Photonics Spectra*, 35(10), 96-104.

Gryczynski, I., Malicka, J., Gryczynski, Z., Geddes, C. D. and Lakowicz, J. R. (2002) The CFS engineers the intrinsic radiative decay rate of low quantum yield fluorophores, *J. Fluorescence*, 12(1), 11-13.

Malika, J., Gryczynski, I., Maliwal, B. P., Fang, J. F. and Lakowicz, J. R. (2003). Fluorescence spectral properties of cyanine dye labeled DNA near metallic silver particles, *Biopolymers*, 72(2), 96-104.

Malicka, J., Gryczynski, I., Kusba, J., Shen, Y. B., and Lakowicz, J. R. (2002). Effects of metallic silver particles on resonance energy transfer in labeled bovine serum albumin, *Biochem. Biophys. Res. Comm.*, 294(4), 886-892.

Gryczynski, I., Malika, J., Shen, Y. B., Gryczynski, Z., and Lakowicz J. R. (2002). Multiphoton excitation of fluorescence near metallic particles: Enhanced and localized excitation, *J. Phys. Chem. B.*, 106(9), 2191-2195.

Malika, J., Gryczynski, I., Fang, J. Y., Kusba, J. and Lakowicz, J. R. (2002). Photostability of cy3 and cy5-labeled DNA in the presence of metallic silver particles, *J. Fluorescence*, 12(3-4), 439-447.

Geddes, C. D., Cao, H., Gryczynski, I., Gryczynski, Z., Fang, J. and Lakowicz, J. R. (2003). Metal-enhanced Fluorescence (MEF) Due to silver colloids on a planar surface: Potential applications of Indocyanine green to in vivo imaging, *J. Phys Chem. A.*, 107, 3443-3449.

Geddes, C. D., Parfenov, A., Gryczynski, I., Malicka, J., Roll, D., and Joseph R. Lakowicz, (2003). Fractal silver structures for metal-enhanced fluorescence: Applications for ultra-bright surface assays and lab-on-a-chip based nanotechnologies, *J. Fluorescence*, 13(2), 123-128.

Geddes, C. D., Parfenov, A., and Lakowicz, J. R., (2003). Photodeposition of silver can result in Metal-enhanced fluorescence, *Applied Spectroscopy*, 57(5), 526-531.

Geddes, C. D., Gryczynski, I., Malicka, J., Gryczynski, Z., and Lakowicz, J. R. (2003). Metal-Enhanced Fluorescence: Potential applications in HTS, *Combinatorial Chemistry and HTS*, 6(2), 109-117.

Lakowicz, J. R., Gryczynski, I., Malicka, J., Gryczynski, Z., and Geddes, C. D. (2002). Enhanced and localized multi-photon excited fluorescence near metallic silver islands: Metallic islands can increase probe photostability *J. Fluorescence*, 12(3/4), 299-302.

Aslan, K., Lakowicz, J. R., and Geddes, C. D., (2005). Rapid Deposition of Triangular Silver Nanoplates on Planar Surfaces: Application to Metal-enhanced Fluorescence, *Journal of Physical Chemistry B.*, 109(13), 6247-6251.

Aslan, K., Lakowicz, J. R., and Geddes, C. D., (2005). Fast and slow deposition of Silver Nanorods on Planar-Surfaces: Application to Metal-enhanced fluorescence. *Journal of Physical Chemistry B.*, 109(8), 3157-3162.

Aslan, K., Lakowicz, J. R., Szmacinski, H., and Geddes, C. D., (2005). Enhanced ratiometric pH sensing using SNAFL-2 on silver island films: Metal-enhanced fluorescence sensing. *Jn. Fluorescence*, 15(1), 37-40.

Wu, M., Lakowicz, J. R., and Geddes, C. D., (2005). Enhanced lanthanide luminescence using silver nanostructures: Opportunities for a new class of probes with exceptional spectral characteristics. *Jn. Fluorescence*, 15(1), 53-59, 2005.

Aslan, K., Lakowicz, J. R., Szmacinski, H., and Geddes, C. D., (2004). Metal-enhanced fluorescence solution based sensing Platform. *Jn. Fluorescence*, 14 (6), 677-679, 2004.

Geddes, C. D., Parfenov, A., Roll, D., Gryczynski, I., Malicka, J., and Lakowicz, J. R., (2004). Roughened silver electrodes for use in Metal-enhanced fluorescence. *Spectrochemica Acta A.*, 60 (8-9), 1977-1983.

Parfenov, A., Gryczynski, I., Malicka, J., Geddes, C. D., and Lakowicz, J. R., (2003). Enhanced fluorescence from fluorophores on fractal silver surfaces. *Jn. Phys. Chem. B.*, 107(34), 8829-8833.

Pugh, V. J., Szmacinski, H., Moore, W. E., Geddes, C. D., and Lakowicz, J. R., (2003).Submicrometer spatial resolution of Metal-enhanced fluorescence. *Applied Spectroscopy*, 57(12), 1592-1598.

Geddes, C. D., Parfenov, A., Roll, D., Fang, J., and Lakowicz, J. R., (2003). Electrochemical and laser deposition of silver for use in metal-enhanced fluorescence. *Langmuir*, 19, 6236-6241.

Lakowicz, J. R., Geddes, C. D., Malicka, J., Gryczynski, K., Lukomska, J. Huang, C., Aslan, K., and Gryczynski. I., (2004). Advances in Surface-enhanced Fluorescence. *Jn. Fluorescence*, 14(4), 425-441.

Aslan, K., et at and Geddes, C. D., (2005) Metal-enhanced fluorescence: An emerging tool in biotechnology. *Current opinions in Biotechnology*, 16(1), 55-62.

Geddes, C. D., Aslan, K., Gryczynski. I., Malicka, J., and Lakowicz, J. R., Radiative Decay Engineering (RDE). *Topics in Fluorescence Spectroscopy Volume 8*, Edited by Chris D. Geddes and Joseph R. Lakowicz, Springer, New York, pp. 405-448.

Geddes, C. D., Aslan, K., Gryczynski. I., Malicka, J., and Lakowicz, J. R., (2004) Noble-metal surfaces for Metal-enhanced fluorescence, In *Reviews in Fluorescence 2004*, Ed by Chris D. Geddes and Joseph R. Lakowicz, Kluwer Academic Plenum Publishers, New York, pp. 365-401. ISBN: 0-306-48460-9.

Aslan, K., Bagugu, R., Lakowicz, J. R., and Geddes, C. D., (2005). Metal-Enhanced Fluorescence from Plastic substrates. *Jn. Fluorescence*, 15(2), 99-104.

Lakowicz, J. R., Malicka, J., Gryczynski. I., Gryczynski. Z., Geddes, C. D., (2003) Radiative Decay Engineering: The role of photonic mode density in biotechnology. *Jn. Physics D. Appl. Phys.* 38, R240-249.

Hansen, T.W., (1996). Therapeutic approaches to neonatal jaundice: an international survey. *Clin Pediatr.* 35(6):309-316.

Amin, S.B., Ahlfors,,C., Orlando, M.S., Dalzell, L.E., Merle, K.S., Guillet, R., (2001). Bilirubin-albumin binding variables in premature infants. *Pediatrics* 107(4):664-668.

Cashore, W.J., Oh, W., (1982). Unbound bilirubin and kernicterus in low birth weight infants. *Pediatrics* 69(4):481-485.

Nakamura, H., Takada, S. Shimabuku, R., et al. (1985). Auditory nerve and brainstem responses in newborn infants with hyperbilirubinemia. *Pediatrics*. 75:703-708.

(56) References Cited

OTHER PUBLICATIONS

Funato, M., Tamai, H., Shimada, S., et al. (1994) Vigintiphobia, unbound bilirubin, and auditory brainstem responses. *Pediatrics*. 93:50-53.

Jacobsen, J. and Wennburg, P., (1974). Determination of Unbound Bilirubin in the Serum of Newborns. *Clin. Chem*. 20(7): 783-789.

Ahlfors, C., (1981). Effect of Serum Dilution on Apparent Unbound Bilirubin Concentration as Measured by the Peroxidase Method. *Clin. Chem*. 27(5): 692-696.

Ahlfors, C., (2000).Measurement of Plasma Unbound Unconjugated Bilirubin. *Anal. Biochem*. 279: 130-135.

Blackmon, L.R., Fanarof,f A.A., and Raju, T.N.K., (2004). Research on prevention of bilirubin-induced brain injury and kernicterus: National Institute of Child Health and Human Development Conference Executive Summary. *Pediatrics* 114:229-233.

Fleischmann, M., Hendra, P. J., and McQuillan, A. J. (1974). Raman spectra of pyridine absorbed at a silver electrode, *Chem. Phys. Lett*., 26(2), 163-166.

Jeanmaire, D. L. and Van Duyne, R. P. (1997). Surface Raman spectroelectrochemistry. Part 1. Heterocyclic, aromatic and aliphatic amines adsorbed on the anodised silver electrode, *J. Electroanal. Chem*., 84, 1-20.

Aroca, R., Jennings, C., Kovacs, G. J., Loutfy, R. G. and Vincett, P. S. (1985). Surface-enhanced Raman scattering of Langmuir-Blodgett monolayers of phthalocyanine by indium and silver island films, *J. Phys. Chem*., 89, 4051-4054.

DeSaja-Gonzalez, J., Aroca, R., Nago, Y. and DeSaja, J. A. (1997). Surface enhanced fluorescence and SERS spectra of N-octadecyl-3,4:9,10-perylenetetracarboxylic monohydride on silver island films, *Spectrochim. Acta*. Part A, 53, 173-181.

Hildebrandt, P. and Stockburger, M., (1984). *J. Phys Chem. B*., 88, 5935.

Kneipp, K., Wang, Y., Kneipp, H., Itzkan, L., Dasari, R. R. and Feld, M. S., (1996). *Phys. Rev. Lett*., 76, 2444.

Kneipp, K., Wang, Y., Kneipp, H., Perelman, L. T., Itzkan, L., Dasari, R. R., and Feld, M. S., (1997). *Phys. Rev. Lett*., 78, 1667.

Wokaun, A., Lutz, H.-P., King, A. P., Wild, U. P. and Ernst, R. R. (1983). Energy transfer in surface enhanced fluorescence, *J. Chem. Phys*., 79(1), 509-514.

Holland, W. R. and Hall, D. G. (1985). Waveguide mode enhancement of molecular fluorescence. *Optics Letts*., 10(8), 414-416.

Glass, A. M., Liao, P. F., Bergman, J. G. and Olson, D. H. (1980). Interaction of metal particles with adsorbed dye molecules: absorption and luminescence. *Optics Letts*., 5(9), 368-370.

Benner, R. E., Dornhaus, R. and Chang, R. K. (1979). Angular emission profiles of dye molecules excited by surface lasmon waves at a metal surface, *Optics Commun*., 30(2), 145-149.

Barnes, W. L. (1998). Fluorescence near interfaces: The role of photonic mode density, *J. Modern Optics*, 45(4), 661-699.

Camplon, A., Gallo, A. R., Harris, C. B., Robota, H. J. and Whitmore, P. M. (1980). Electronic energy transfer to metal surfaces: A test of classical image dipole theory at short distances, Chem. *Phys. Letts*., 73(3), 447-450.

Sokolov, K., Chumanov, G. and Cotton, T. M. (1998). Enhancement of molecular fluorescence near the surface of colloidal metal films, *Anal. Chem*., 70, 3898-3905.

Hayakawa, T., Selvan, S. T. and Nogami, M. (1999). Field enhancement effect of small Ag particles on the fluorescence from $Eu^{3+}$-doped $SiO_2$ glass, *Appl. Phys. Lett*., 74(11), 1513-1515.

Geddes, C. D., Cao, H., and Lakowicz, J. R. (2003). Enhanced photostability of ICG in close proximity to Gold colloids, *Spectrochemica Acta A*. 59, 2611-2617.

Selvan, S. T., Hayakawa, T. and Nogami, M. (1999). Remarkable influence of silver islands on the enhancement of fluorescence from $Eu^{3+}$ ion-doped silica gels, *J. Phys. Chem. B*., 103, 7064-7067.

Strickler, S. J. and Berg, R. A. (1962). Relationship between adsorption intensity and fluorescence lifetime of molecules, *J. Chem. Phys*., 37, 814-822.

Rivas, L., Sanchez-Cortes, S., Garcia-Ramos, J. V. and Morcillo, G. (2001). Growth of silver colloidal particles obtained by citrate reduction to increase the Ramen enhancement factor, *Langmuir*, 17(3), 574-577.

Shirtcliffe, N., Nickel, U. and Schneider, S. (1999). Reproducible preparation of silver sols with small particle size using borohydride reduction:For use as nuclei for preparation of larger particles, *J. Colloid Interface Sci*., 211(1), 122-129.

Pastoriza-Santos, I., and Liz-Marzan, L. M. (2000). Reduction of silver nanoparticles in DMF. Formation of monolayers and stable colloids, *Pure Appl. Chem*., 72(1-2), 83-90.

Pastoriza-Santos, I., Serra-Rodriguez, C. and Liz-Marzan, L. M. (2000). Self-assembly of silver particle monolayers on glass from $Ag^+$ solutions in DMF, *J. Colloid Interface Sci*., 221(2), 236-241.

Bright, R. M., Musick, M. D. and Natan, M. J. (1998). Preparation and characterization of Ag colloid monolayers, *Langmuir*, 14(20), 5695-5701.

Ni, F. and Cotton, T. M. (1986). Chemical procedure for preparing surface-enhanced Raman scattering active silver films, *Anal. Chem*., 58(14), 3159-3163.

Freeman, R. G., Grabar, K. C., Allison, K. J., Bright, R. M., Davis, J. A., Guthrie, A. P., Hommer, M. B., Jackson, M. A. , Smith, P. C., Walter, D. G. and Natan, M. J. (1995). Self-assembled metal colloid monolayers: An approach to SERS substrates, *Science*, 267, 1629-1632.

Grabar, K. C., Freeman, R. G., Hommer, M. B. and Natan, M. J. (1995). Preparation and characterisation of Au colloid monolayers, *Anal. Chem*., 67, 735-743.

Link, S. And El-Sayed, M. A. (1999). Spectral properties and relaxation dynamics of surface plasmon electronic oscillations in gold and silver nanodots and nanorods, *J. Phys. Chem. B*., 103, 8410-8426.

Kreibig, U. and Genzel, L. (1985). Optical absorption of small metallic particles, *Surface Science*, 156, 678-700.

Krelbig, U., Gartz, M. and Hilger, A. (1997). Mie resonances: Sensors for physical and chemical cluster interface properties, *Ber. Bunsenges, Phys. Chem*., 101(11), 1593-1604.

Toshima, N. and Yonezawa, T. (1998). Bimetallic nanoparticles-novel materials for chemical and physical applications, *New J. Chem*., 1179-1201.

Caruso, F., Caruso, R. A. and Mohwald, H. (1998). Nanoengineering of inorganic and hybrid hollow spheres by colloidal templating, *Science*, 282, 1111-1114.

Yee, J. K., Parry, D. B., Caldwell, K. D. and Harris, J. M. (1991). Modification of quartz surfaces via thiol-disulphide interchange, *Langmuir*, 7, 307-313.

Farmer, S. C. and Patten, T. E. (2000). Synthesis of luminescent organic/inorganic polymer nanocomposites, *Polym. Mater. Sci. Eng*., 82, 237-238.

Comor, M. I. and Nedeljkovic, J. M. (1999). Enhanced photocorrosion stability of colloidal cadmium sulphide-silica nanocomposites, *J. Mater. Sci. Lett*., 18, 1583-1585.

Gryczynski, I., Malicka, J., Nowaczyk, K., Gryczynski, Z., and Lakowicz, J. R. (2004). Effects of Sample thickness on the Optical Properties of Surface Plasmon-Coupled Emission. *J. Phys Chem. B*., 108, 12073- 12083.

Gryczynski, I., Malicka, J., Gryczynski, Z., Nowaczyk, K., and Lakowicz, J. R. (2004). Ultraviolet Surface Plasmon-Coupled Emission Using Thin Aluminum Films. *Anal. Chem*., 76(21), 4076-4081.

Geddes, C. D., Douglas, P., Moore, C.P., Wear, T.J., Egerton, P.L., (1999) Optical thin film sensors for the determination of aqueous halide Ions. *Jn. Fluorescence*, 9(3), 163-171, 1999.

Geddes, C. D. (2000) Optical thin film polymeric sensors for the determination of aqueous chloride, bromide and iodide ions at high pH, based on the quenching of fluorescence of two acridinium dyes. *Dyes and Pigments*, 45(3), 243-251.

Geddes, C. D. (2000) A Halide sensor based on the quenching of fluorescence of an immobilised indolium salt. *Photochemistry and Photobiology A: Chemistry*, 137(2-3), 145-153.

Geddes, C. D.(2001) Halide sensing using the SPQ molecule. *Sensors and Actuators Chemical*, 72(2), 188-195.

Mills, A., and Chang, Q., (1994). Colorimetric polymer film sensors for dissolved carbon dioxide. *Sensors and Actuators B:Chemical*, 21, 83-89.

(56) References Cited

OTHER PUBLICATIONS

Herrero, M., Tiemblo, P., Reyes-Labarta, J., Mijangos, C., and Reinecke, H., (2002) PVC modification with new functional groups. Influence of hydrogen bonds on reactivity, stiffness and specific volume. *Polymer*, 43, 2631-2636.

Yu, Z.J., Kang, E.T., Neoh, K.G., and Tan, K.L., (2001) Surface Passivation of epoxy resin with a covalently adhered poly(tetrafluoroethylene) layer. *Surface & Coatings Technology*, 138, 48-55.

Endo, K., (2002) Synthesis and Structure of poly(vinyl chloride). *Progess in Polymer Science*, 27, 2021-2054.

James, N.R., and Jayakrishnan, A., (2003). Surface thiocyanation of plasticized poly(vinyl chloride) and its effect on bacterial adhesion. *Biomaterials*, 24, 2205-2212.

Liu, B., Yang, Y., Zhao-Yang, W., Wang, H., Shen, G., and Yu, R., (2005) A potentiometric acetylcholinesterase biosensor based on plasma-polymerized film. *Sensors and Actuators B:Chemical*, 104, 186-190.

Geddes, C. D., Parfenov, A., and Lakowicz, J.R. (2003) Luminescent Blinking from Noble-metal Nanostructures: New Probes for localization and imaging. *Jn. Fluorescence*, 13(4), 297-299.

Geddes,C.D.,Parfenov, A., Gryczynski, I., and Lakowicz,J.R.(2003) Luminescent blinking from silver nanostructures.*Jn. Phys. Chem. B.* 107(37), 9989-9993.

Geddes,C.D.,Parfenov,A.,Gryczynski, I., and Lakowicz, J.R., (2003) Luminescent blinking of gold nanoparticles. *Chem. Phys. Letts*, 380(3-4), 269-272, 2003.

Geddes,C.D., (2001) Optical halide sensing using fluorescence quenching: Theory, simulations and applications—A review. An invited review article commissioned by the *Institute of Physics. Meas. Sci. Technol.*, 12(9), R53-R88.

Matveeva, E., Gryczynski, Z., Malicka, J., Gryczynski, I., and Lakowicz, J. R. (2004) Metal-enhances fluorescence immunoassays using total internal reflection and silver island-coated surfaces. *Anal. BioChem.*, 334, 303-311.

Malicka, J., Gryczynski, I., Gryczynski, Z., and Lakowicz, J. R. (2004) Use of Surface Plasmon-Coulped Emission to measure DNA Hybridization. *Journal of Biomolecular screening.* 9(3), 208-214.

Matveeva, E., Gryczynski, Z., Gryczynski, I., Malicka, J., and Lakowicz, J. R. (2004) Myoglobin Immunoassay Utilizing Directional Surface Plasmon-Coupled Emission. *Anal. Chem.*, 76(21), 6287-6292.

Matveeva, E., Malicka, J., Gryczynski, I., Gryczynski, Z., and Lakowicz, J. R. (2004) Multi-wavelength immunoassays using surface plasmon coupled emission. *Biochemical and Biophysical Research Communications.*, 313, 721-726.

Ludbrook, J., (2002) Statistical Techniques for Comparing Measurers and Methods of Measurement: A Critical Review. *Clin. and Expt Pharm. and Physiol.* 29: 527-536.

Wilson, G.M.; Deeley, R.G. (1995) An Episomal Expression Vector System for Monitoring Sequence-Specific Effects on mRNA Stability in Human Cell Lines. *Plasmid*, 33:198-207.

Kindler, S.; Wang, H.; Richter, D.; Tiedge, H. (2005) RNA Transport and Local Control of Translation. *Annu. Rev. Cell. Dev. Biol*, 21:223-45.

Call, D.R.; Borucki, M.K.; Loge, F.J. (2003) Detection of Bacterial Pathogens in Environmental Samples Using DNA Microarrays. *J.Microbiol. Methods*, 53, 235-243.

Bustin, S.A. (2002) Quantification of mRNA Using Real-Time Reverse Transcription PCR (RT-PCR): Trends and Problems. *J. Mol. Endocrinol.* 2002, 29, 23-39.

Tsai, S.P., Wong, A., Mai, E., Chan, P., Mausisa, G., Vasser, M., Jhurani, P., Jakobsen, M.H., Wong, W.L.T., and Stephan, J.-P. (2003) Nucleic acid capture assay, a new method for direct quantitation of nucleic acids. *Nucleic Acids Res.* 31:e25.

Aslan, K.; Gryczynski I.; Malicka J.; Matveeva E.; Lakowicz, J.R.; Geddes, C.D. (2005) Metal-enhanced fluorescence: an emerging tool in biotechnology. *Current Opinion in Biotechnology*, 16(1), 55-62.

Parfenov, A.; Gryczynski, I.; Malicka, J.; Geddes, C.D.; Lakowicz, J.R. (2003) Enhanced Fluorosense from Fluorophores on Fractal Silver Surfaces. *J. Phys. Chem. B.*, 107: 8829-8833.

Malicka, J.; Gryczynski, I.; Gryczynski, Z.; Lakowicz J.R. (2004) Use of Surface Plasmon-Coupled Emission to Measure DNA Hybridization. *J. Biomol Screen.*, 9(3), 208-215.

Sastry, M.; Mayya, K.S.; Bandyopadhyay, K. (1997) pH Dependent Changes in the Optical Properties of Carboxylic Acid Derivatized Silver Colloidal Particles. *Coll. Surf. A*, 127 (1-3): 221-228.

Aslan, K.; Geddes, C D. (2005) Microwave-Accelerated Metal-Enhanced Fluorescence: Platform Technology for Ultrafast and Ultrabright Assays, *Anal. Chem.*, 77(24), 8057-8067.

Aslan, K.; Leonenko, Z.; Lakowicz, J.R.; Geddes, C.D. (2005) Annealed Silver-Island Films for Applications in Metal-Enhanced Fluoresence: Interpretation in Terms of Radiating Plasmons *J. Fluores*, 15(5):643-654.

Aslan,K.; Geddes, C.D. (2006) Microwave-Accelerated Metal-Enhanced Fluorescence (MAMEF): Application to Ultra Fast and Sensitive Clinical Assays. *J. Fluores.*, 16:1.

Aslan, K.; Holley, P.; Geddes, C.D. Microwave-Accelerated Metal-Enhanced Fluorescence (MAMEF) with silver colloids in 96-well plates: Application to ultra fast and sensitive immunoassays, High Throughput Screening and Drug Discovery. *J. Immun. Methods* (Submitted).

Xie, H.; Yu, Y.H.; Xie, F.; Lao, Y.Z.; Gao, Z. (2004) A Nucleic Acid Biosensor for Gene Expression Analysis in Nanograms of mRNA. *Anal. Chem.*, 76, 4023-4029.

Amin, S.B., (2004). Clinical assessment of bilirubin-induced neurotoxicity in premature infants. *Seminars in Perinatology* 28:340-347.

O'Shea, T.M., Dillard, R.G., Klinepeter, K.L., Goldstein, D.J., (1992). Serum bilirubin levels, intracranial hemorrhage, and the risk of developmental problems in very low birth weight neonates. *Pediatrics*. 90(6):888-892.

Ritter, D.A., Kenney, J.D., Norton, H.J., Rudolph, A.J., (1982). A prospective study of free bilirubin and other risk factors in the development of kernicterus in premature infants. *Pediatrics* 69(3):260-266.

Axelrod, D., Burghardt, T. P. and Thompson, N. L. (1984). Total internal reflection fluorescence, *Ann. Rev. Biophys. Bioeng.*, 13, 247-268.

Knudsen, A., Pedersen, A.O., Brodersen, R., (1986). Spectroscopic Properties of Bilirubin-Human Serum Albumin Complexes: A Stoichiometric Analysis. *Arch. Biochem and Biophys.* 244(1): 273-284.

Lamola, A., Eisinger, J., Blumberg, W., Patel S., Flores J., (1979). Fluorometric Study of the Partition of Bilirubin among Blood Components: Basis for Rapid Microassays of Bilirubin Binding Capacity in Whole Blood. *Anal. Biochem.*100:25-42.

Ludbrook, J., (1997). Comparing methods of measurement. *Clin. and Expt Pharm. and Physiol.* 24: 193-203.

van Doorn, L.J.; Kleter, B.; Voermans, J.; Maertens, G.; Brouwer, H.; Heijtink, R.; Quint, W. (1994) Rapid Detection of Hepatitis C Virus RNA by Direct Capture from Blood. *J. Med. Virol*. 42: 22-28.

Wilson, G.M., and Deeley, R.G. (1995) An episomal expression vector system for monitoring sequence-specific effects on mRNA stability in human cell lines. *Plasmid* 33:198-207.

Amin, S.B., Charafeddine, L., Guillet, R., (2005) Transient Bilirubin Encephalopathy and Apnea of Prematurity in 28 to 32 Weeks Gestational Age Infants. *J Perinatol*. 2005.

Pledger, D.R., Scott, J., Belfield, A., (1982) Kernicterus at low levels of serum bilirubin: The impact of bilirubin albumin -binding capacity. *Biol Neonate*. 1982; 41:38-44.

Garziani, L.J., Mitchell, D.G., Kornhauser, M., et al., (1992) Neurodevelopment of preterm infants. Neonatal neurosonographic and serum bilirubin studies. *Pediatrics*. 89(2):229-234.

Van de Bor, M., Dokkum, M.E., Schreuder, A.M., Veen, S., Brand, R., Verloove-Vanhorick, S.P., (1992) Hyperbilirubinemia in low birth weight infants and outcome at 5 years of age. *Pediatrics*. 89(3):359-364.

Bratlid, D. (1990). How bilirubin gets into the brain. *Clin Perinatol*. 17:449-465.

(56) References Cited

OTHER PUBLICATIONS

Ahlfors, C.E. (2001). Bilirubin-albumin binding and free bilirubin. *J. Perinatol.* 21: S40-42.

Nakamura, H., Yonetani, M., Uetani, Y., Funato, M., Lee, Y., (1992). Determination of serum unbound bilirubin for prediction of kernicterus in low birth weight infants. *Acta. Paediatr. Jpn.* 34:642-647.

Berde, C., Benitz, W., Rasmussen F., et al., Bilirubin Binding in the Plasma of Newborns: Critical Evalutation of a Fluorescence Quenching Method and Comparison to the Peroxidase Method., (1984) *Pediatric Research.* 18(4): 349-354.

Geddes, C. D., and Douglas, P., (2005). Fluorescent dyes bound to hydrophilic copolymers—Applications for aqueous halide sensing. *App. Poly. Sci.*, 76(5), 603-615, 2000.

Krumlauf, R. Analysis of Gene Expression by Northern Blot. *Mol. Biotechnol.*, 1994, 2, 227-242.

Elkahloun, A.G.; Gaudet, J.; Robinson, G.S.; Sgroi. D.C. In situ Gene Expression Analysis of Cancer Using Laser Captiure Microdissection Microassays and Real Time Quantitative PCR. *Cancer Biol. Ther.* 2002,1, 354-358.

Ramaswamy, S.; Golub, T.R. (2003) DNA Microarrays in Clinical Oncology. *J. Clin. Oncol.*, 2003, 20, 1932-1941.

Haines, D.S.; Gillespie, D.H. RNA Abundance Measured by a Lysate RNAse Protection Assay. *Biotechniques* 1992, 12, 736-741.

Rosenau, C.; Kaboord, B.; Qoronfleh. M.W. (2002) Development of a Chemiluminescence—Based Ribonuclease Protection Assay. *Biotechniques*, 33: 1354-1358.

Lakowicz, J. R., Malicka, J., Gryczynski, Z., Huang, J., Geddes, C. D. and Gryczynski, I., (2003), Increased sensitivity of Fluorescence detection, *PharmaGenomics*, 3(3), 38-46.

Pettinger, B., and Gerolymatou, A. (1984). Dyes adsorbed at Ag-colloids: Substitution of fluorescence by similarly efficient surface fluorescence and surface Raman scattering, *Ber. Bungens. Phys. Chem.*, 88, 359-363.

Porter, E, and Waters, W., (1966). A rapid micromethod for measuring the reserve albumin binding capacity in serum from newborn infants with hyperbilirubinemia. *J. Lab & Clin. Med.* 67(4):660-668.

DeGraff, A., and Demas, J.N., (2005) Luminescence-Based Oxygen Sensors. Reviews in Fluorescence 2005.*Springer*, New York, 125-151.

Aslan, K. et al. Metal—Enhanced Fluorescence-Based Sensing. J. Am. Chem, Soc., 128(13): 4206-4207.

Gryczynski, Z. et al. Metal-Enhanced Fluorescence: A Novel Approach to Ultra-Sensitive Fluorescence Sensing Assay Platforms. Proceedings of the SPIE, vol. 5321, 2004, pp. 275-282.

Lakowicz et al. Advances in Surface-Enhanced Fluorescence, Journal of Fluorescence, vol. 14, No. 4, Jul. 2004, pp. 425-441.

Lakowicz et al. Radioactive Decay Engineering: the Role of Photonic Mode Density in Biotechnology. Journal of Physics D: Applied Physics, vol. 36, 2003, pp. R240-R249.

Malicka, et al. DNA Hybridization Assays Using Metal-Enhanced Fluorescence. Biochemical and Biophysical Research Communications, vol. 306, 2003 pp. 213-218.

Aslan, K., et al and Geddes, C. D., (2005) Metal-enhanced fluorescence: An emerging tool in biotechnology. *Current opinions in Biotechnology*, 16(1), 55-62.

G. Bauer, F. Pittner and Th. Schalkhammer, Metal Nano-Cluster Biosensors, Mikrochim. Acta 131, 107-114 (1999).

Th. Schalkhammer, Metal Nano Clusters as Transducers for Bioaffinity Interactions, Monatschefte für Chemie 129, 1067-1092 (1998).

\* cited by examiner

- : 484-mer RNA

- TAMRA-Labeled 15-mer Oligo

- : Thiolated 15-mer Oligo

- : Silver Island Films

METAL ENHANCED FLUORESCENCE-BASED SENSING METHODS

CROSS-REFERENCE TO RELATED APPLICATION

This application is a Continuation Application claiming priority to U.S. patent application Ser. No. 11/917,804, filed on Jul. 21, 2008, now U.S. Pat. No. 7,939,333, which in turn claims priority to PCT Application No. PCT/US2006/023738 filed in the U.S. Patent and Trademark Office, PCT Division, on Jun. 19, 2006, which in turn claims priority to U. S Provisional Patent Application No. 60/691,851 filed on Jun. 17, 2005 and U. S Provisional Patent Application No. 60/781,933 filed on Mar. 13, 2006 wherein the contents of the above-identified applications are hereby incorporated by reference herein for all purposes, and is a Continuation-in-Part application of U.S. patent application Ser. No. 10/536,502 filed on Dec. 14, 2005, now U.S. Pat. No. 8,114,598, which in turn claimed priority to International Patent Application No. PCT/US2003/038163 filed on Nov. 26, 2003, which in turn claimed priority to U.S. Provisional Patent Application No. 60/429,263 filed on Nov. 26, 2002.

GOVERNMENT RIGHTS IN INVENTION

Work related to the invention was conducted in the performance of NIH R21 GM070929. As a result of such contracts, the U.S. Government has certain rights in the invention described herein.

BACKGROUND OF THE INVENTION

1. Field of the Invention

The present invention relates to detection methods, and more particularly, to the use of metallic surfaces to enhance intensity of fluorescence species or reactions in capture assays thereby increasing the sensitivity and rapidity of these assays. The present invention is applicable for determining free unbound bilirubin in serum and for capturing nucleotide sequences.

2. Background of the Related Art

Assays are used widely for the detection and determination of a variety of proteins, peptides and small molecules. Currently, there exists a large diverse family of assays today and the basic principles are generally the same. These assays typically use receptor-ligand binding for target molecule recognition and fluorescence based readouts for signal transduction. Fluorescent based assay systems are available in many forms, such as time-resolved assays, energy transfer assays and fluorescence polarization assays.

Fluorescence detection is the basis of most assays used in drug discovery and high throughput screening (HTS) today. In all of these assays, assay rapidity and sensitivity is a primary concern. The sensitivity is determined by both the quantum yield of the fluorophores and efficiency of the detection system, while rapidity is determined by the physical and biophysical parameters of temperature, concentration, assay bioaffinity, etc.

Heretofore, assay methods and/or systems have been lacking in sensitivity for determining and quantifying the amount of free unbound bilirubin in neonatal serum or isolating target nucleotide sequence.

Technology has been developed that recognizes that close-proximity to noble metallic surfaces can alter the radioactive decay rate and/or excitation rate of fluorophores. Further, it has been shown that quantum yield of low quantum yield fluorophores can be increased by proximity to such metallic surfaces. However, the use of such technology, termed Metal Enhance Fluorescence (MEF), has been limited and heretofore has not been envisioned for the use of determining the level of free unbound bilirubin in neonatal serum or for isolating a desired nucleotide sequence.

The most commonly used method for serum free-bilirubin measurement is the peroxidase method. The concentration of unbound bilirubin is determined from the peroxidase-catalyzed oxidation of bilirubin by a peroxide [47]. The protocol for measurement of free bilirubin according to the peroxidase method requires a blood sample to be drawn from the baby. The serum, the portion of the sample to be tested, is then separated by centrifugation. The serum is taken on ice and shielded from the light, and is used to measure free bilirubin using the unbound bilirubin UB Analyzer, a direct free bilirubin measurement. The UB Analyzer (FDA approved) in essence utilizes the peroxidase method, but in a standardized instrument. First, a measurement is performed using the full concentration of the peroxidase enzyme, and a readout is obtained which indicates both total and free bilirubin levels. A second measurement is performed using half the initial concentration of peroxidase. To improve the accuracy of the free bilirubin measurement, both the readouts are used to derive the final estimated value of free bilirubin using a known algorithm table.

However, the UB Analyzer has some technical pitfalls including the need for reagent manipulation and sample dilution before analysis. A 40-fold dilution must be made to the serum sample, which can alter intrinsic bilirubin binding properties and mask the presence of binding competitors to albumin. Moreover, there is a possibility of interference with free bilirubin measurement by direct or conjugated bilirubin [48]. The test also requires the use of at least two peroxidase concentrations in order to improve the accuracy of the free bilirubin measurement, as an estimate of the equilibrium free bilirubin in the sample being measured. This necessary and repeated measurement with two different peroxidase concentrations increases both the amount of blood and time required for each sample. Furthermore, the light absorption of bilirubin varies with the type of albumin present and the number of bilirubin molecules bound per albumin. There are also factors that can cause the overestimation or underestimation of the free bilirubin measurement, depending on the rate of the peroxidase reaction [49].

There are also several other cumbersome techniques that indirectly measure unbound bilirubin. For example, the HBABA method, utilizes 2-(4'-hydroxybenzeneazo) benzoic acid to measure the available albumin binding sites of a sample, by a shift in the absorbance spectrum of the dye when bound to albumin [50]. This gives an estimate of how much bilirubin is unbound. The fluorescence-quenching method allows the determination of the binding capacity and affinity of albumin, whereby the concentration of unbound bilirubin may be indirectly calculated, based on the quenching of the ultraviolet fluorescence of albumin upon binding to bilirubin [51].

Providing a sensitive and reliable assay for determining serum free bilirubin would be of great value because jaundice (unconjugated hyperbilirubinemia) is one of the most common problems of prematurity. Almost all premature babies have some degree of jaundice during their first week. Jaundice can lead to neurotoxicity including deafness, auditory neuropathy, athetoid cerebral palsy, supranuclear gaze palsy, neonatal seizures, and apnea [31-33]. Premature infants are at a higher risk of bilirubin-induced neuronal injury than term infants [34]. To prevent bilirubin-induced neurotoxcity, neonates are often treated with intensive phototherapy. In rare cases with severe hyperbilirubinemia and unresponsiveness to phototherapy, exchange transfusion is used. Uniform guidelines, however, do not exist for the management of unconjugated hyperbilirubinemia in premature infants. Currently, serum total bilirubin levels are used to evaluate and manage premature infants with unconjugated hyperbilirubinemia. However, there is substantial evidence that serum total bilirubin levels correlate poorly with bilirubin-induced neurotoxicity in premature infants [35-37]. Moreover, institutional variations in the levels of bilirubin at which phototherapy and exchange transfusions are initiated in jaundiced premature newborns indicate that the current management of hyperbilirubinemia in these babies is not evidence based [38].

Various biochemical factors are involved in the pathogenesis of bilirubin encephalopathy. Bilirubin binding is a complex function of the concentrations of total bilirubin, free unbound bilirubin and serum albumin. According to current theory, unbound bilirubin (UB; also referred to as non-albumin-bound or free bilirubin) is capable of crossing the intact blood brain barrier and causing subsequent neuronal damage [39]. Current literature supports the notion that the risk of bilirubin neurotoxicity increases with increasing free bilirubin (or UB) concentration. According to "free bilirubin thinking," the free bilirubin concentration determines the distribution of bilirubin between the tissues and vascular space [40]. There exists overwhelming clinical evidence to support this free bilirubin theory [41-46]. Studies in neonates supporting free bilirubin theory have involved autopsy findings of kernicterus, and auditory brainstem response (ABR) findings of transient bilirubin encephalopathy. The findings of these studies have suggested that the neurological outcome of hyperbilirubinemia correlate better with free bilirubin than total serum bilirubin levels. In premature infants, overt kernicterus becomes likely with unbound bilirubin levels ≥15 nmol/L (0.87 µg/dl) [42-43], and ABR changes are seen at unbound bilirubin levels >0.5 µg/dl [41]. In term neonates, ABR changes are seen at unbound bilirubin levels >1.0 µg/dl [45]. In summary, as far as the available biochemical measures are concerned, most of the published studies indicate that free bilirubin is the most sensitive biochemical measure to evaluate premature infants with jaundice.

Due to the shortcomings of the techniques discussed above, it would be advantageous to have a system for measuring unbound bilirubin that not only directly measures the metal-amplified fluorescence of the unbound bilirubin itself but also provides a direct correlation between the fluorescence emission and the concentration of the free bilirubin, even in whole unseparated blood.

Notably, the present invention also addresses the problems relating to isolation and quantitation of specific nucleotide sequences, such as RNA molecules, from biological samples. Isolating and determining a specific nucleotide sequence is an essential tool for the study of regulated gene expression [119] and is routinely employed in studies of gene transcription, [120] RNA stability, [121] RNA transport and a host of other biological processes [122]. In addition, RNA detection and quantitation also present an appealing strategy for rapidly identifying unknown biological agents (bacterial, viral, etc.) [123, 124]. Furthermore, nucleotide sequence detection is of great utility for gene expression profiling in clinical settings, where the expression of a subset of genes within tissue (i.e. biopsy) or blood samples may be rapidly measured, revealing diagnostic information to direct patient-specific therapeutic strategies [120, 125].

All current techniques for quantifying specific RNAs exploit base-pair complimentarity between a target RNA and one or more nucleic acid probes, either in the form of extended DNA or RNA sequences including Northern blots, [119]; RNase protection assays, [126, 127]; [RPAs]) or short oligonucleotides (reverse transcription-PCR [RT-PCR], [128]; or RNA capture assays [129]. This principle allows for extremely precise target recognition, yet current methods of probe:target hybrid detection face a number of technological restrictions. In particular, the utility of RNA sensing in microbial detection and/or clinical gene expression profiling may be hindered by two principal constraints, namely: sensitivity and rapidity [130].

RNA capture assays offer a simple and rapid approach to RNA quantitation. Target RNAs are selected based on complimentarity to an oligonucleotide probe which is attached to a solid surface or matrix, then detected by annealing a radio- or chemically-labeled probe at a distinct site on the target RNA [129]. At present, however, these assays are subject to the same sensitivity limitations as those described for Northern blots and RPAs, namely, that detection relies on the activity of radiolabels, the sensitivity of conjugated fluorophores, or the use of bright secondary chemiluminescent assays. These conditions make RNA capture assays currently useful only for abundant RNA species, thus limiting their general utility as a biosensor platform [128].

Thus, there is a need for biosensor systems and methods of using same that overcome the shortcomings of the prior art and provide for increased sensitivity and signal production for use in determining free bilirubin in blood or serum, and isolating target nucleotide sequences.

SUMMARY OF INVENTION

In one aspect, the present invention relates to a metallized surface micro-assay based detection system for determining unbound bilirubin in neonatal serum in the presence of a predominantly high background of bilirubin bound Human Serum Albumin (HSA). The system comprises a polymeric material which is coated and/or at least surface impregnated with HSA that is applied over the metallized surface for capture of unbound bilirubin.

In another aspect, the present invention relates to a metallized surface assay based detection system for determining unbound bilirubin in neonatal serum, the detection system comprising:
  a. metallic particles or film deposited on a substrate surface; and
  b. a polymeric film positioned on the metallic particles or metallic film, wherein at least the surface of the polymeric film is impregnated with HSA in an amount sufficient to capture of unbound bilirubin.

In yet another aspect, the present invention relates to a detection system for determining free unbound bilirubin, the system comprising:
  a. a metallic material applied to at least a portion of a substrate surface;
  b. a polymeric layer applied to the metallic material and any exposed substrate surface to form a detection substrate, wherein the polymeric layer is coated with and/or at least surface impregnated with human serum albumin (HSA) in an amount sufficient to bind with free bilirubin;
  c. a source of electromagnetic energy for applying energy to the detection system; and
  d. a detector for measuring fluorescence emission of the bound bilirubin in the polymeric material, wherein the polymeric layer is of sufficient thickness to position the bound bilirubin a distance from the metallic surface to enhance fluorescence.

Preferably, the thickness of the polymeric layer is from about 20 nm to about 300 nm, and more preferably from about 40 nm to about 120 nm.

The metallic material may take the form of metallic islands, colloids, nanostructures of any geometric shape, porous matrix or a continuous metallic surface. The metallic element may include any form of noble metals such as silver, gold, platinum and copper, and more preferably, the metallic material is gold or a low density silver. The substrate positioned beneath the metallic material may include glass and/or a polymeric material.

The HSA impregnated and/or coated polymeric material may further include a tag that emits a radiative signal when excited by electromagnetic energy. Still further, the system may include a fluorophore having binding affinity for the bound bilirubin that provides a fluorescence signal and an enhanced signal when positioned a sufficient distance from the metallic material.

In a still further aspect, the present invention relates to a method of detecting unbound bilirubin in neonatal serum, the method comprising:
  a. contacting a detection substrate with neonatal serum, wherein the detection substrate comprises:
    i. metallic material applied to at least a portion of a substrate surface; and
    ii. a polymeric layer applied to the metallic material, wherein the polymeric layer is coated with and/or at least surface impregnated with human serum albumin in an amount sufficient to bind with free bilirubin;
  b. applying a source of electromagnetic energy to the detection substrate; and
  c. detecting fluorescence emission of the bilirubin bound on the human serum albumin and/or in the polymeric material, wherein the free bilirubin diffuses into the polymeric material and its intrinsic fluorescence is enhanced by positioning near the metallic material.

Another aspect of the present invention relates to a target nucleotide sequence sensing platform comprising:
  a. a glass or polymeric substrate at least partially coated with metallized material, wherein the metallized material comprises an anchor probe;
  b. a first probe having binding affinity for the target nucleotide sequence and comprising a fluorophore;
  c. a second probe having binding affinity for the target nucleotide sequence nucleotide sequence, wherein the second probe binds to a different region of the target nucleotide sequence and at a predetermined distance from the first probe and wherein the second probe comprises a linking molecule having binding affinity for the anchor probe;
  d. a first annealing solution for binding the first and second probes to any target nucleotide sequence in the sample;
  e. a second annealing solution for binding the linking molecule to the anchor probe; and
  f. a single or multiple photon excitation system for exciting the fluorophore label.

In yet another aspect, the present invention relates to a method for capturing a target RNA in a sample, the method comprising:
  a. providing a metallized surface at least partially coating a substrate, wherein the metallized surface further comprises an anchor probe;
  b. preparing a first nucleotide sequence probe essentially complementary to the target RNA for binding to one area of the target RNA, wherein the first probe comprises a fluorescence label;
  c. preparing a second nucleotide sequence probe essentially complementary to the target RNA, wherein the second nucleotide probe binds to a region of the target RNA sequence different from and at a predetermined distance from the binding of the first probe and wherein the second probe comprises a linking molecule having binding affinity for the anchor probe;
  d. providing annealing conditions for binding the first and second nucleotide sequence probes to any target RNA in the sample; and
  e. providing annealing conditions for binding the linking molecule to the anchor probe, wherein the linking molecule is positioned a sufficient distance from the fluorescence label to position the fluorescence label a distance from the metallized surface for enhanced fluorescence upon single or multiple photon excitation.

The excitation energy may be generated by any electromagnetic energy source having the ability to generate single or multiple photons, and preferably, generated by a laser diode, light emitting diode source or pulsing systems thereof.

The metallized surface may take the form of metallic islands, nanostructures, colloids, porous matrix or a continuous metallic surface. The metallic element may include any form of noble metals such as silver, gold, platinum and copper, and more preferably, the metallic material is a low density silver. The substrate that comprises the metallized surface may include glass or polymeric material, or combinations thereof.

In a still further aspect, the present invention relates to a target RNA sensing platform comprising:
  a. a glass or polymeric substrate at least partially coated with metallized material, wherein the metallized material comprises an anchor probe;
  b. a first DNA probe having binding affinity for the target RNA and comprising a fluorescence label.
  c. a second DNA probe having binding affinity for the target RNA, wherein the second DNA probe binds to a different region of the target RNA sequence and at a predetermined distance from the first DNA probe and wherein the second probe comprises a linking molecule having binding affinity for the anchor probe;
  d. a first annealing solution for binding the first and second DNA probes to any target RNA in the sample;
  e. a second annealing solution for binding the linking molecule to the anchor probe; and
  f. a single or multiple photon excitation system for exciting the fluorescence label.

Another aspect relates to a kit for use in determining free unbound bilirubin in a test sample of neonatal serum, the kit comprising
  a. a metallic material applied to at least a portion of a substrate surface, wherein the substrate surface is positioned within a container; and
  b. a polymeric layer applied to the metallic material surface to form a detection substrate, wherein the polymeric layer is coated and/or at least surface impregnated with human serum albumin (HAS) in an amount sufficient to bind with free bilirubin, wherein the polymeric layer is of sufficient thickness to position any bound bilirubin a sufficient distance from the metallic material to enhance fluorescence.

The metallic material may take the form of metallic islands, colloids, nanostructures of any geometric shape, porous matrix or a continuous metallic surface. The metallic material may include any form of a noble metal such as silver, gold, platinum, copper and combinations thereof, and more preferably, the metallic material is gold or a low density silver. The substrate positioned beneath the metallic material may include glass and/or a polymeric material.

Other features and advantages of the invention will be apparent from the following detailed description, drawings and claims.

DETAILED DESCRIPTION OF THE INVENTION

Figure 1:
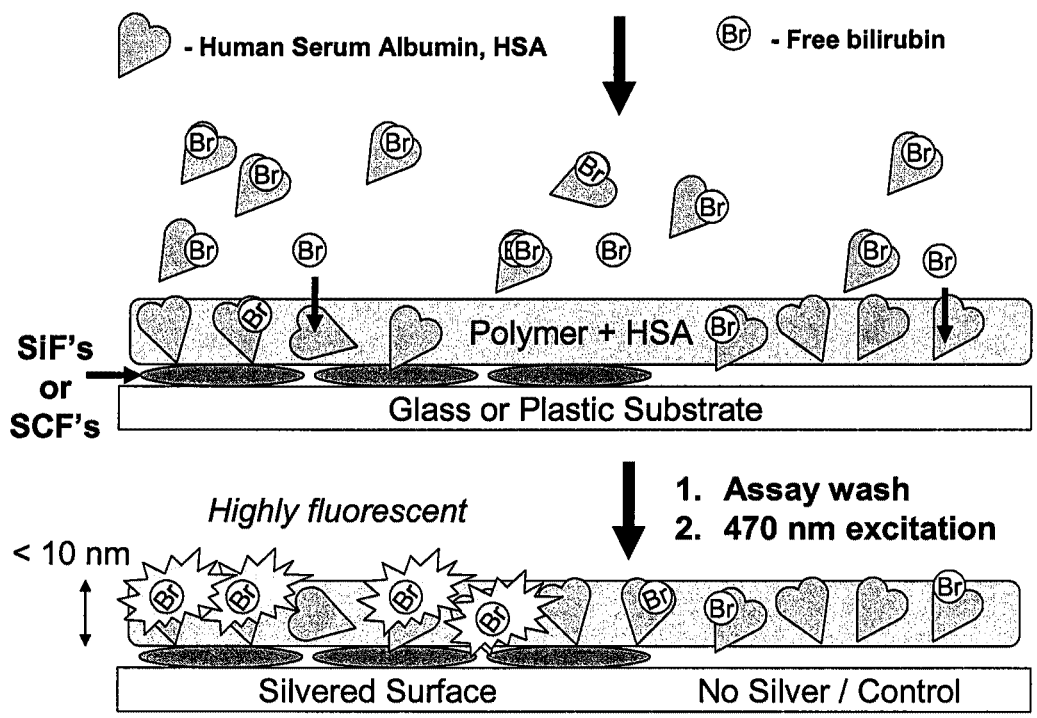
FIG. 1 shows the MEF free unbound bilirubin assay of the present invention.

The present invention provides assays utilizing Metal-Enhanced Fluorescence (MEF) for detection, isolation and/or amplification of free unbound bilirubin or target nucleotide sequences.

Most knowledge relating to fluorescence is based on measurements of the spectroscopic properties of fluorophores that upon excitation, radiate into a homogeneous and non-conducting medium, typically referred to as free space. These spectral properties are well described by Maxwell's equations for a radiating oscillating dipole. However, the interactions of an emitting dipole with physical objects can be considerably more complex, as known from antenna and receiver design. The size and shape of an antenna are designed with the goal of directing the radiation and accounting for its interactions with the earth's surface. A fluorophore is also like an antenna, but one, which oscillates at high frequency and radiates short wavelengths. Local effects are not usually seen because of the small size of fluorophores relative to the experimental apparatus.

However, literature is rapidly starting to emerge whereby nearby conducting metallic surfaces can respond to a fluorophores oscillating dipole and modify the rate of emission, that is the intrinsic radiative decay rate, and the spatial distribution of the emitted radiation. Theoreticians describe this effect as due to changes in the photonic mode density near the fluorophore [30]. In most spectroscopic measurements, the solution or medium is transparent to both the emitted and sampling radiation. However, there are several important exceptions to the free space condition. One well-known example is Surface Enhanced Raman Scattering (SERS) [53-57]. It is known that the presence of a metallic surface can enhance the Raman signals by factors of $10^3$ to $10^8$, and reports of even larger $10^{14}$-$10^{16}$ fold enhancements have appeared [58-60]. The presence of a nearby metal film, island or particle can also alter the emission properties of fluorophores. The most well known effect is the quenching of fluorescence by a near-by metal. The emission of fluorophores within 50 Å of a metal surface is almost completely quenched. This effect is used in fluorescence microscopy with evanescent wave excitation. The emission from membranes cellular regions near the quartz-water interface is quenched, allowing selective observation of the emission from the cytoplasmic region more distance from the solid-liquid interface [61]. In addition to quenching, it is known that metal surfaces or particles can cause significant increases in fluorescence. Remarkably, depending on the distance and geometry, metal surfaces or particles can result in enhancement factors of many 1000 fold for the fluorescence emission [62-64].

Fluorophores near a metal film are not expected to emit isotropically, but rather the emission is directed into selected directions that depends on the sample configuration and the nature of the metallic surface [65-70]. In addition to directionality, the decay times of fluorophores are altered by the metal and under certain conditions can lead to an enhanced photostability of fluorophores [71].

Figure 2:
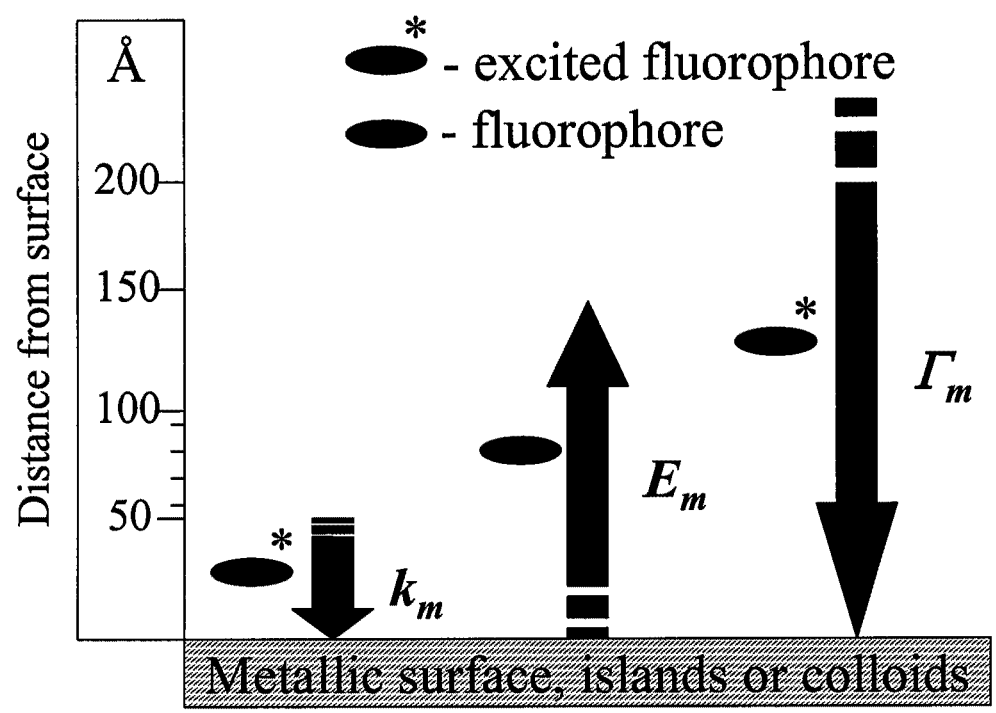
FIG. 2 shows the effects of local metallic structures on a nearby fluorophore.
Figure 3:
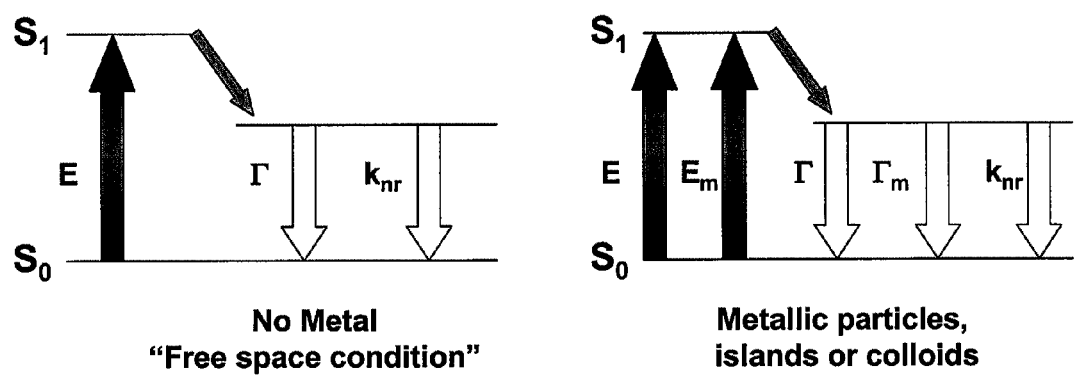
FIG. 3 shows a classical Jablonski diagram for the free space condition and the modified from in the presence of metallic particles, islands or colloids. E—Excitation. $\Gamma_m$—radiative rate in the presence of metal.

The effects of metallic particles and surfaces on fluorophores are due to at least three known mechanisms as shown in FIG. 2. One is energy transfer quenching, $k_m$, to the metal with a $d^{-3}$ dependence [68]. This quenching can be understood by damping of the dipole oscillations by the nearby metal and as mentioned above, typically occurs within about 30 to 50 Å of the surface. A second mechanism is an increase in the emission intensity due to the metal increasing the local incident field on the fluorophore, $E_m$, with a maximum theoretical enhancement effect of 140. This effect has been observed for metal colloids and is appropriately called the "Lightening Rod effect" [69, 70, 72]. This enhancement can be understood as due to the metal particles on concentrating the local field and subsequently increasing the rate of excitation. The third mechanism is that a nearby metal can increase the intrinsic decay rate of the fluorophore, $\Gamma_m$, that is, to modify the rate at which a fluorophore emits photons [1-30]. The last two fluorophore-metal interactions offer remarkable opportunities for advanced fluorescence assay technology, and is the major focus of the present invention and heretofore have not been utilized in assays for clinical sensing.

"Fluorophore," and "fluorescence label," used interchangeably herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3' dipropylthiadicarbocyanine (diS-C$_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrirmidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Also included are novel quaternary nitrogen heterocyclic boronic acid-containing compounds including:

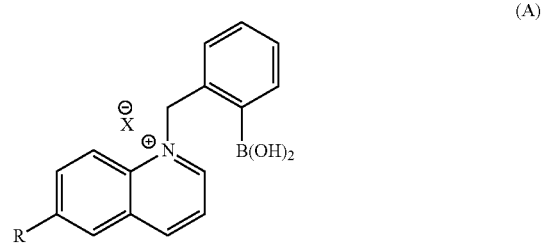

(A)

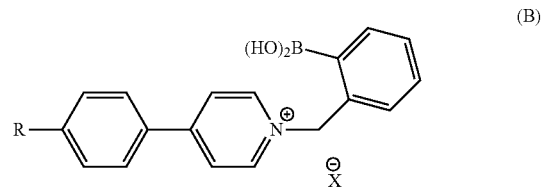

(B)

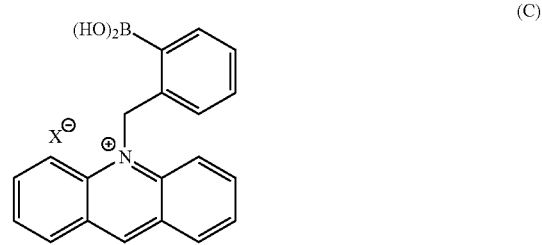

(C)

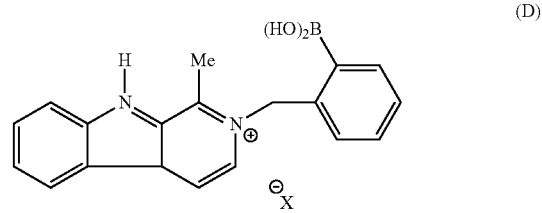

(D)

(E)

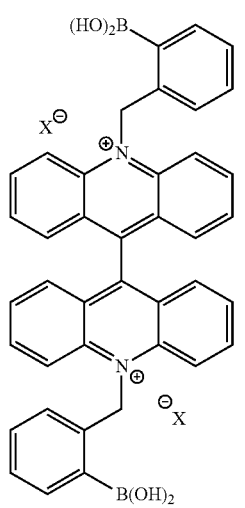

and

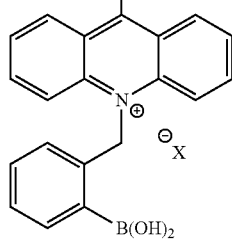

(F)

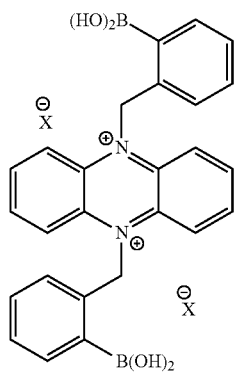

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups.

In one embodiment, the present invention provides enhanced emissions using metallized islands of elliptical, spherical, triangular or rod-like forms. In exemplary cases, the elliptical islands have aspect ratios of 3/2, and the spherical colloids have diameters of 20-60 nm. However, the invention is not limited to any particular geometry. Using known coating techniques, the placement of metallic islands could be controlled precisely, as close as 50 nm apart. In the continuous metallic film case, the fluorophore emissions could be detected in the analyte solution up to 500 nm away from the surface of the metal. In the case where the metallic coating is formed by islands, the enhanced fluorophore emissions could be detected in the solution up to 200 nm away from the surface of the metal.

In another embodiment, the present invention provides for metallic material and a fluorophore label capable of fluorescing, wherein the metallic material and the fluorophore are separated by at least one film spacer layer. The thickness of said film may be chosen so as to enhance the fluorescence of the fluorophore due to the distance of the fluorophore from the metallic material. The film spacer layer may be one or multiple layers of a polymer film, a layer formed from a fatty acid or a layer formed from an oxide. In a preferable embodiment, the film spacer layers and the metallic material are chemically inert and do not bind to the fluorophore to be detected or to intermediates that are bound to the compounds to be detected, for example covalently bound. The layer formed from a fatty acid may be formed by a Langmuir-Blodgett technique. The film spacer layer may be a spin coated polymer film. The oxide layer may be formed from a deposition technique, such as vapor deposition.

Further, the metallic material may be in the form of a porous three dimensional matrix. The three dimensional matrix may be a nano-porous three dimensional matrix. The metallic material may include metal colloid particles and/or metal-silica composite particles. The metallic material may comprise agglomerated metal particles and/or binary linked particles or metal particles in a polymer matrix. The three dimensional matrix may be formed from controlled pore glasses or using matrices assembled from the aggregation of silver-silica composites themselves. The matrices may be metallic nanoporous matrix, through which species will flow and be both detected and counted more efficiently.

It is known that a nearby metal can increase the intrinsic decay rate of a fluorophore, that is, to modify the rate at which the fluorophore emits photons. In fluorescence, the spectral observables are governed by the magnitude of λ, the radiative rate, relative to the sum of the non-radiative decay rates, $k_{nr}$ such as internal conversion and quenching.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The emission enhancement may be observed at distances according to the type of fluorophore to be detected and the type, shape of the metal material, noting a difference between a film and a metallic island or colloid. For example, emission enhancement may be observed when a fluorophore distances about 4 nm to about 200 nm to metal surfaces. Preferable distances are about 4 nm to about 30 nm, and more preferably, 4 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Different surface enhanced fluorescence effects are expected for mirrors, sub-wavelength or semi-transparent metal surfaces, silver island films or metal colloids. More dramatic effects are typically observed for islands and colloids as compared to continuous metallic surfaces. The silver islands had the remarkable effect of increasing the intensity 5-fold while decreasing the lifetime 100-fold. Such an effect can only be explained by an increase in the radiative decay rate.

Fluorescence can be detected using devices including, but not limited to, a spectrofluorometer having a light source and detector. Additional detectors may include GaAs-cathode PMT. Further detectors may include photomultiplier tubes. Additionally, it is advantageous for the device to have a monochromator so that specific wavelengths of light may be used to excite a molecule or to detect emissions at a specific wavelength.

Excitation light sources can include arc lamps and lasers, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a fluorophore absorbs two photons simultaneously, it will absorb enough energy to be raised to an excited state. The fluorophore will then emit a single photon with a wavelength that depends on the fluorophore used and typically in the visible spectra. The use of the Ti-sapphire laser with infrared light has an added benefit, that being, longer wavelengths are scattered less, which is a benefit to high-resolution imaging. Importantly, there is reduced background signal level gained by using 2-photon excitation as compared to 1-photon excitation by utilizing localized excitation near by a metallic particles.

When a sample containing a fluorophore is placed in the spectrofluorometer and exposed to an amount of exciting radiation, the fluorophore emits radiation that is detected by a photomultiplier tube. The fluorescence intensity of a fluorophore can be increased in response to an amount of exciting radiation when the distance between the metal particle and the fluorophore is from about 4 nm to about 2000 nm, preferably from about 40 nm to about 200 nm. The enhancement of fluorescence is, in part due to the localized excitation of the fluorophores when in close proximity to the silver nanoparticles and results in improved photostability of the fluorophores [131, 132]. When the metal (silver, aluminum or gold) is a continuous 45 nm-thick film, the spatially isotropic fluorescence emission can be converted into directional emission towards a detector further improving the detectability [134].

In applications of MEF, it was found that the enhanced fluorescence signals (Quantum yields—Qm) of fluorophores in close proximity (<10 nm) to metallic nanostructures could be well described by the following equations:

$$Q_m = (\Gamma + \Gamma_m)/(\Gamma + \Gamma_m + k_{nr}) \quad (1)$$

where $\Gamma$ is the unmodified radiative decay rate, $\Gamma_m$ is the metal-modified radiative decay rate and $k_{nr}$ are the non-radiative rates. Similarly, the metal-modified lifetime, $\tau m$, of a fluorophore is decreased by an increased radiative decay rate:

$$\tau_m = 1/(\Gamma + \Gamma_m + k_{nr}) \quad (2)$$

These equations have resulted in most unusual predictions for fluorophore-metal combinations, and it is these predictions and observations that are currently finding profound implications and applications in fluorescence based nanotechnology. From equations 1 and 2, it can be seen that as the value of $\Gamma$m increases, the quantum yield Qm increases, while the lifetime, $\tau$m, decreases. This is contrary to most observations in fluorescence where the free-space quantum yield, $Q_0$, and lifetime, $\tau_0$, usually change in unison as described by the well known equations:

$$Q_0 = \Gamma/(\Gamma + k_{nr}) \quad (3)$$

$$\tau_0 - 1/(\Gamma + k_{nr}) \quad (4)$$

In addition, one major criterion for choosing fluorophores in current immunoassays has been a high quantum yield. This can lead to a high background from either unlabelled fluorophores or a high fluorescence background from non-specific assay absorption. However, metal-enhanced fluorescence is ideally suited in this regard, in that low quantum yield fluorophores are more favorable, the fluorescence enhancement factor in the presence of silver nanostructures given by $1/Q_0$ where $Q^0$ is the free-space quantum yield in the absence of metal. Subsequently MEF when applied to immunoassays, yields ultra bright assays, with a much higher Signal:Noise as compared to identical assays not employing the MEF phenomenon.

Preparation of Metal Islands

Metallic island particles are prepared in clean beakers by reduction of metal ions using various reducing agents. For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Preparation of Silver Colloids

Colloids can be prepared as suspensions by citrate reduction metals. Preferred metals are silver and gold. Again, gold may be used because of the absorption of gold at shorter wavelengths. However, gold colloids may also be used with longer wavelength red and NIR fluorophores. The size of the colloids and their homogeneity can be determined by the extensive publications on the optical properties of metal particles available and the effects of interface chemistry on the optical property of colloids.

Silver island films can be formed by a chemical reduction of a silver salt on the quartz surface, which are relatively simple to fabricate. However, this approach does not provide a control of particle size, or distance of the fluorophores from the surface. Enhancements of 1000 fold have been with the realization that sample geometries have been heterogeneous and the enhancement factors spatially averaged.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.

Positioning of the biomolecule or metal particle at a desired distance can be achieved by using a film. The film may be a polymer film, a Langmuir-Blodgett film or an oxide film.

Langmuir-Blodgett Films

Metal-fluorophore distances may be achieved by using Langmuir-Blodgett films with fatty acid spacers. The fatty acids may be from natural sources, including concentrated cuts or fractionations, or synthetic alkyl carboxylic acids. Examples of the fatty acids include, but not limited to, caprylic ($C_8$), capric ($C_{10}$), lauric ($C_{12}$), myristic ($C_{14}$), palmitic ($C_{16}$), stearic ($C_{18}$), oleic ($C_{18}$), linoleic ($C_{18}$), linolenic ($C_{18}$), ricinoleic ($C_{18}$) arachidic ($C_{20}$), gadolic ($C_{20}$), behenic (C22) and erucic ($C_{22}$). The fatty acids with even numbered carbon chain lengths are given as illustrative though the odd numbered fatty acids can also be used.

Metal-fluorophore distances may be achieved by using polymer films. Examples of the polymer include, but not limited to, polyvinyl alcohol (PVA). Absorbance measurements and ellipsometry may be used to determine polymer film thickness. One type of polymer films is spin coated polymer film. The technology of spin coated polymer spacer films readily allows films to be coated onto a variety of surfaces, with varied thickness from >0.1 um. The coating can be performed on a spin coater, which allows uniform surface thickness by varying polymer concentration (viscosity) and spin speed. For example, Model P6700 spin coater (Specialty Coating Systems Inc.), allows uniform surface thickness by varying polymer concentration (viscosity) and spin speed.

Metallic colloids (or various other non-spherical shapes/particles) may also be incorporated into organic polymers, covalently or non-covalently, to form polymeric matrices, wherein the distance from diffusing species affords an increase in radiative decay rate and thus, an increase in quantum yield. Such polymeric matrices are ideal for sensing/flowing sensing applications of low concentration species.

Polymers containing metal particles may have other applications, including but not limited to, size inclusion/exclusion sensing of a fluorescent or a non-fluorescent species, increased photostability of embedded fluorophores, single pore single molecule detection, and porous polymers which allow diffusing analytes or antibodies, resulting in a detectable and quantifiable signal change in the analyte or antibody or respective transduction element.

FIG. 1 illustrates the new assay for the detection of unbound bilirubin in neonatal serum. Briefly, the new assay, as shown in FIG. 1, provides for immobilizing noble metallic nanostructures on either glass or plastic supports. A thin polymeric layer is then coated and immobilized on both the metallized and nonmetallized portions of the glass/plastic supports. The polymeric film contains an optimized amount of HSA (Human Serum Albumin) to bind any unbound bilirubin. The molecular weight of the polymer has been chosen such that small molecules, like bilirubin, can readily diffuse into the polymer film and bind with HSA, but once bound can't diffuse out from the film due to the crosslinking density and therefore pore size of the polymer. The polymer film also prevents bilirubin bound HSA from diffusing into the polymer film. In essence, the polymer films acts as a membrane through which only free bilirubin diffuses. Free bilirubin is typically weakly fluorescent and for the most part considered to be non-fluorescent [74]. However, upon complexation with HSA becomes fluorescent, and due to the close proximity of the silver, is further fluorescently enhanced.

The albumin bound bilirubin on the surface of the polymer is washed away before measurements, providing for enhanced fluorescence intensities from the polymer immobilized free bilirubin fraction of the sample.

The silver surfaces required for MEF and the present assay can be obtained using silver metal island films (SiFs), sandwiched films or even spin coated silver islands or colloids. A quartz surface or plastic may be used as substrates for forming the metal islands thereon. If quartz is used, the quartz slides are soaked in 10 parts 98% $H_2SO_4$ and 1 part 30% $H_2O_2$ for at least 24 hrs. The SiFs are prepared in clean beakers by reduction of silver ions using various reducing agents [75]. Sodium hydroxide is added to a rapidly stirred silver nitrate solution forming a brown precipitate. Ammonium hydroxide is added to redissolve the precipitate. The solution is cooled and dried quartz slides are added to the beaker, followed by glucose. After stirring for 2 mins the mixture is warmed to 30° C. After 10-15 min the mixture turns yellow-green and becomes cloudy. A thin film of silver particles has formed on the slides as can be seen from their brown green color. The slides are rinsed in pure water prior to the experiment. Additional procedures for preparing silver and gold particles are also available [76-80], but primarily silver is used because of the longer surface plasmon absorption of gold, which accounts for its familiar color. It is also possible to silanize (and uniformly amino coat) the slides by placing them in a 2% solution (v/v) of 3-aminopropyltrimethoxysilane (APS) in dry methanol for 2 hrs, rinsed and then air-dried. The silanized substrates should be used within one hour or stored under a dry nitrogen atmosphere. Silver nanostructures readily bind to surface amino groups with high affinity [81,82], and therefore this process can be used to produce films, where the silver is tightly surface bound.

While SiFs have been successfully used for MEF studies [2,6,7,9,25], other metallic particles and surfaces may be employed, if required, e.g. colloids can be prepared as suspensions by citrate reduction of silver or gold, where the size of the colloids and their homogeneity can be judged quite simply by the extensive publications on the optical properties of metal particles available [83,84], and the effects of interface chemistry on the optical property of colloids [85]. It is also possible to prepare bimetallic metal nanoparticles [86] or hollow sphere colloids [87]. In addition, the present inventor has recently published two new procedures for the seed-mediated growth and deposition of silver nanorods [17] and nanotriangles [16] on substrates, and these may be employed, if required. Pre-formed metal particles or colloids can also be bound to glass surfaces by placing functional groups such as cyanide (CN), amine ($NH_2$), or thiol (SH) on a glass or polymer substrate. In this regard, the present inventor has recently shown that MEF can occur from plastic substrates, when inert polymers are firstly functionalized with amino groups [29]. Silver and gold colloids spontaneously bind to such surfaces with high affinity [81,82]. Procedures for coating particles with silica have also been developed and will be used if required [89,90].

Figure 6:
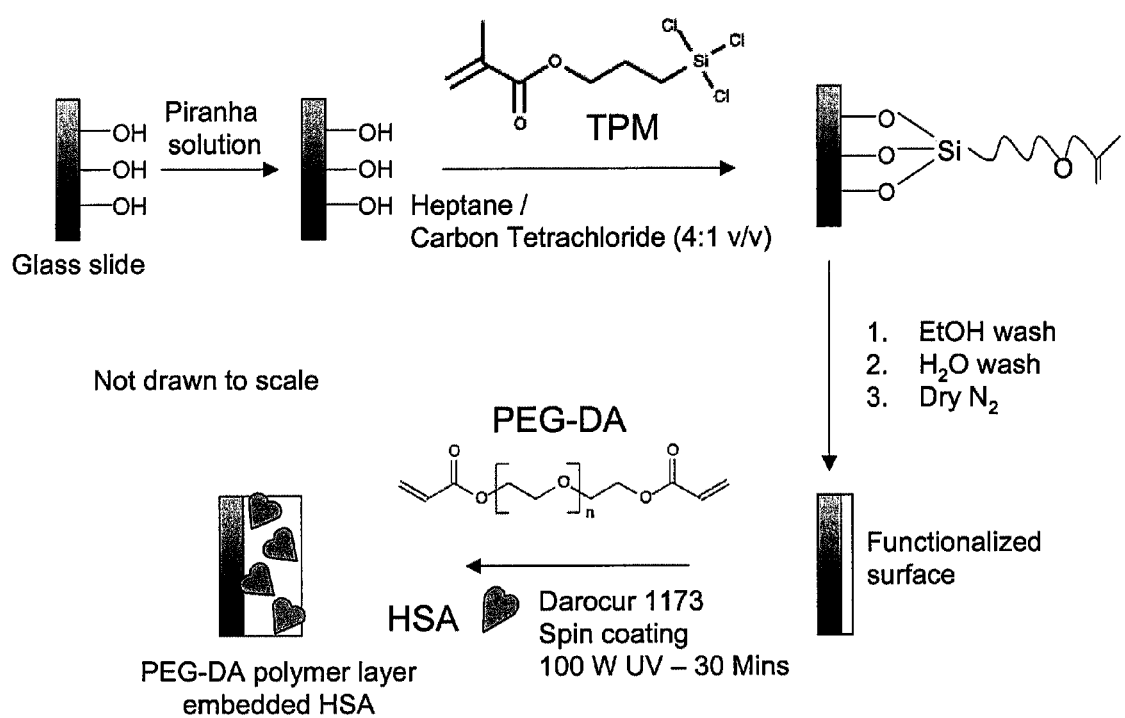
FIG. 6 shows the synthetic scheme for the fabrication of the HSA embedded PEG-DA polymer coating.

In a typical preparation, glass microscope slides, as shown in FIG. 6, were cleaned with "piranha solution" (3:7 30% hydrogen peroxide/concentrated sulfuric acid) for at least 2 hours. Then, the glass substrates were rinsed extensively with deionized water and dried in a stream of dry nitrogen prior to use. The cleaned slides were silanized by immersing them in a solution of 3-((trichlorosiyl)propyl) metacrylate (TPM) in heptane and carbon tetrachloride (4:1, v/v) Then, the TPM-coated glass slides were rinsed in ethanol and then water. Finally, the TPM-coated slides were dried in a stream of nitrogen gas. The polymer precursor solution was prepared by combining 50 mg of PEG-DA (Polyethylene Glycol diacrylate), 200 μL of deionized water, and 6 μL photoinitiator Darocur 1173 (From Ciba Special Chemicals, NY) and vortexing for 5 mins. A few drops of the HSA/Polymer precursor solution was placed on TPM-coated glass slides. Free radical polymerization of the acrylate end groups was initiated by exposure to a 100 W long wave UV spot lamp (UVP Inc.; Upland, Calif.) for 30 min. The thickness of the polymer can be controlled by spin coating before curing [91], and also monitored by a variety of other techniques [91]. In this regard, the CFS is equipped with a Speciality Coating Systems Inc., Model P6700 spin coater, which allows uniform surface thickness by varying polymer concentration (viscosity) and spin speed. This allows polymer film thicknesses down to several nm to be achieved [91,92]. In this regard, film thicknesses are preferably less than 100 nm to optimize MEF, noting that the surface is non continuous and features "valleys and mountains" in its surface topography. The film thickness and HSA ratio is optimize to allow the polymer films to freely diffusing bilirubin, where the film thickness and HSA extent of loading is simply optimized by considering the maximum observable fluorescence intensity at ≈520 nm, the emission maxima for bilirubin. The optimum concentration of HSA is loaded into the polymer precursor solution before spin coating and UV curing. This concentration is optimized with regard to the maximum fluorescence observed by exposure to free solution bilirubin after the polymer is cured. Films are optimized with regard to sensor response times and maximum fluorescence signal. After polymerization, the PEG layer is washed in PBS for at least 2 hours. This step serves to both hydrate the matrix and to remove any unbound surface HSA.

It has been found that the PEG-DA polymer is suitable for the MEF assay. However, other polymers may be used, for example, polymers of HEMA (hydroxy ethyl methacrylate) [93-97], used in the development of aqueous anion sensors [96] and ethyl cellulose [98], used in the construction of dissolved $CO_2$ sensors [98], would be considered. In addition, plasticized PVC is simple to prepare, can be made moderately hydrophilic [99] and can be coated on a variety of surfaces [100-103].

Figure 7:
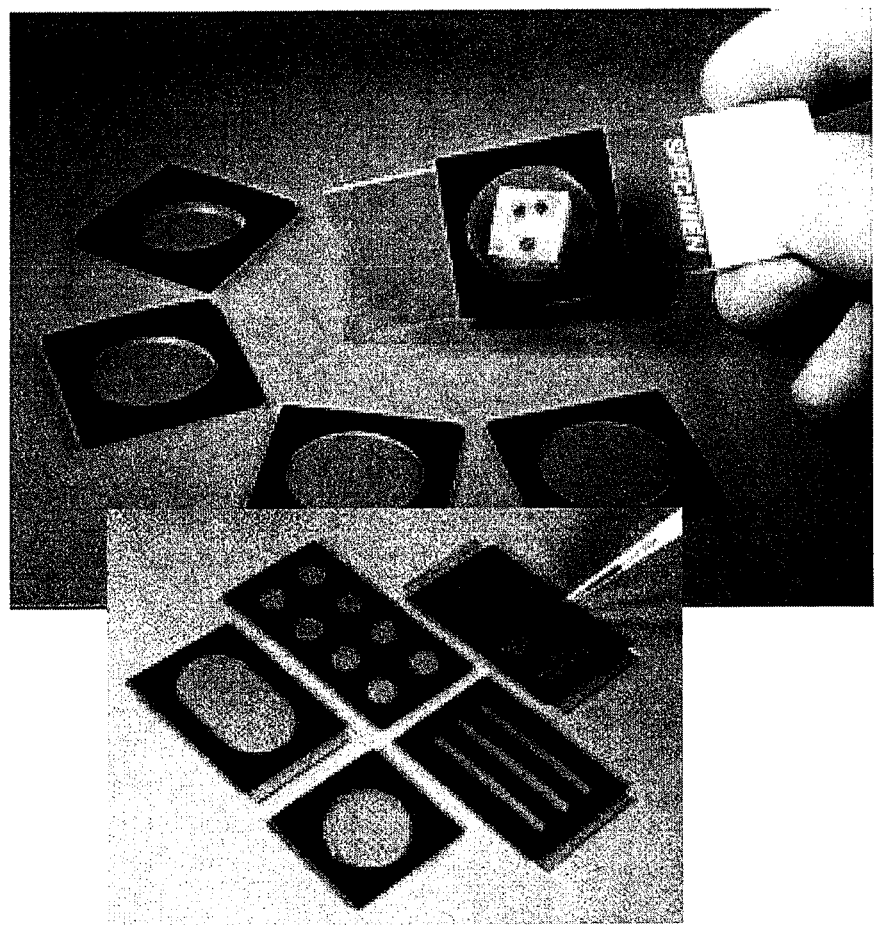
FIG. 7 illustrates representative cover-well micro chambers that readily stick to the surface of many polymers and even glass (wet or dry), can be readily sealed, preventing potential evaporation, trapping a known volume of fluid on the surface of the film. Multiple spot chambers are also available allowing many more measurements per assay.

Free bilirubin calibration plots can be determined for the optimum polymer formulation, which includes the optimized polymer thickness, extent of HSA loading and w/v PEG-DA in the final formulation. These parameters directly affect the free bilirubin diffusion rates into the polymer film (sensor response time) as well as both the enhanced and total fluorescence signal observed. For example, a polymer film 10 μM thick would not be appropriate for a MEF assay, as the MEF phenomenon has been found to occur in a range from 50 to 300 nm from the glass substrate and <10 nm from the peak (top) of the SiFs. Hence, polymer films ranging from about 50 nm to about 300 nm, are deemed appropriate depending on the level of inclusion of HSA in the firm, and preferably, the film is approximately 100 nm thick. 50 μl of buffered free bilirubin solution is pipetted into small micro sample chambers as shown in FIG. 7, which are used to trap small volumes on the assay surface. The emission intensity maxima for bilirubin upon 470 nm laser line excitation, and observed through a Semrock 488 razor edge filter, is recorded. The calibration plots is constructed, using identical assay formulations, starting at the clinically significant concentration 2 μg/dl and decreased through series dilutions (from the master stock solution) until the S/N ratio drops below 3. This value is deemed the highest sensitivity, lowest free bilirubin concentration, the assay can measure. Each concentration is measured four (4) times and the mean value determined and plotted. Preferably, the calibration plot contains no fewer than 25 concentration data points, each the mean of four (4) 4 separate measurements.

Fluorophore or analyte photostability is a primary concern in many applications of fluorescence, particularly platform type assays and single molecule studies [61,107]. The maximum number of photons that are emitted by a fluorophore each second is roughly limited by the lifetime of its excited state. If the silver assay surface decreases the lifetime of bilirubin due its close proximity as suggested by equations 3 and 4, then one can obtain more photons per second per molecule, by appropriately increasing the incident intensity. On the other hand, the MEF effect enhances the intensity while simultaneously shortening the lifetime, so it may in fact be possible to decrease the excitation intensity yet still see a significant increase in the emission intensity and therefore photostability of bound bilirubin. Thus, laser irradiances can be lowered, significantly reducing the likelihood of any bilirubin photochemistries [108,109]. Radiation excitation frequencies are used that do not cause bilirubin photochemical reactions and frequencies such as 516 or 532 nm may be used, by using notch or razor edge filters for emission.

Bilirubin samples were prepared by using a solid, powdered form of bilirubin that can be purchased with high purity from Sigma. Both solid and solutions of bilirubin preferably are kept cold and away from direct light when not in use, due to bilirubin's well-known photochemistries [111]. A stock solution was first prepared by dissolving 1 mg of bilirubin into 10 μl of 1N sodium hydroxide and then 25 μl of 0.1M EDTA to dissolve the bilirubin into a slurry. 3 ml of buffer was then added to equilibrate the pH to ≈7. The concentration of the stock solution was approximately about 500 μM, and from this, dilutions can be made in order to test a range of free bilirubin concentrations. Low concentrations are especially important, because free bilirubin concentration in infants is between 0.05 to 2.5 μg/dl. Both the stock solution and samples to be measured should be kept at 5° C. and wrapped in aluminum foil until use. Samples to be tested, should be prepared on the day of use. The stock bilirubin solution lasts for about a week, one readily observing color change as a function of bilirubin instability [111].

50 μl of buffered free bilirubin was pipetted into a small plastic cover which covers one area of the polymer-coated silvered surface. The small micro-sample chambers, readily available from Invitrogen, as shown in FIG. 7, come in a range of volume sizes from 10's of μl's up to several ml. The sample chambers simply stick to surfaces, retaining and trapping a known surface volume. Typically, a 500 μl blood sample provides ≈250 μl of serum, 50 μl to be used for the new MEF assay.

Figure 4:
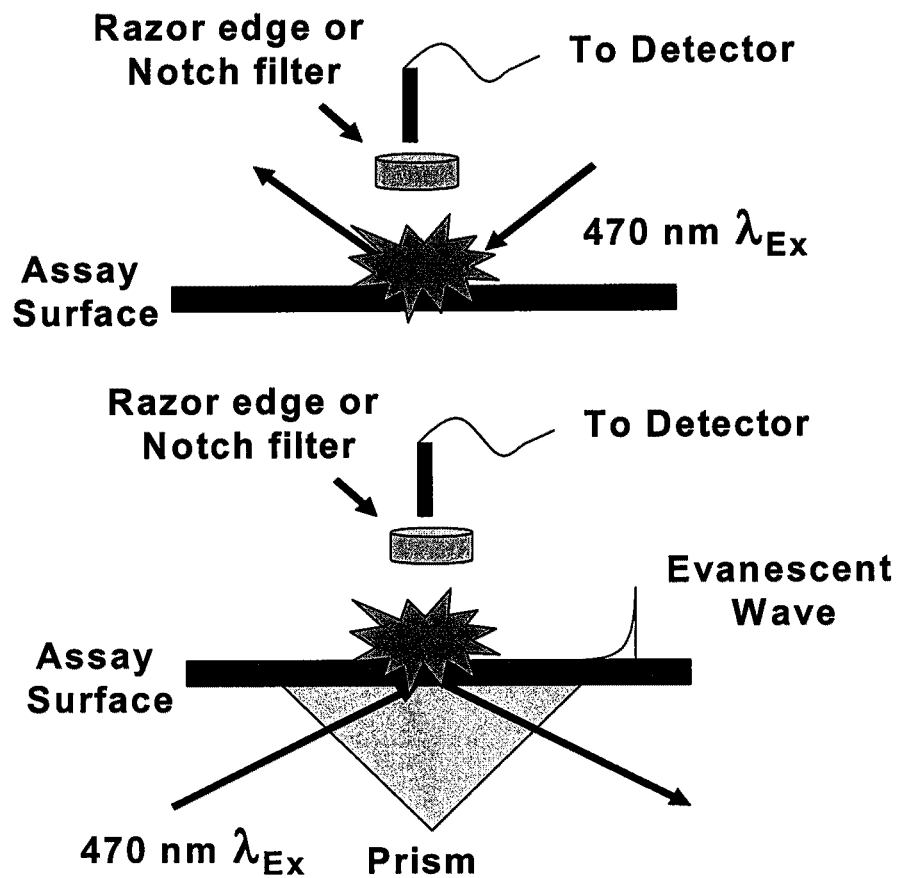
FIG. 4 shows standard front face excitation and off-axis collection of the enhanced intrinsic bilirubin fluorescence, (TOP) and Total-Internal Reflection Fluorescence excitation geometry.

In addition to using standard 470 nm front face excitation and off-axis collection of the enhanced intrinsic bilirubin fluorescence, FIG. 4, the present invention contemplates using a TIRF (Total-Internal Reflection Fluorescence) excitation geometry, but with the same collection angle/geometry for fluorescence. The fluorescence will be collected through a 488 nm Semrock Razor edge filter, the emission spectra collected on a Ocean Optics HR4000 fiber-optic spectrometer. Using a TIRF geometry, as shown in FIG. 4, one produces a metal-amplified evanescent wave above the assay, far greater than is observed than without the silver [113,114], which penetrates several hundred nanometers away from the silver particles [113]. Given the fact that the free bilirubin is in close proximity to the silver particles in the film, then this mode of excitation provides for a good way of suppressing unwanted background fluorescence, as distal material from the silver is not excited and therefore does not fluoresce.

While the surface of the polymer film has shown very little fouling by HSA, (tested using fluorescein labeled HSA from Invitrogen), this approach is still likely to increase the S/N ratio of our system. It is for this reason that TIRF geometries are widely used in many assays today [115,116].

Figure 5:
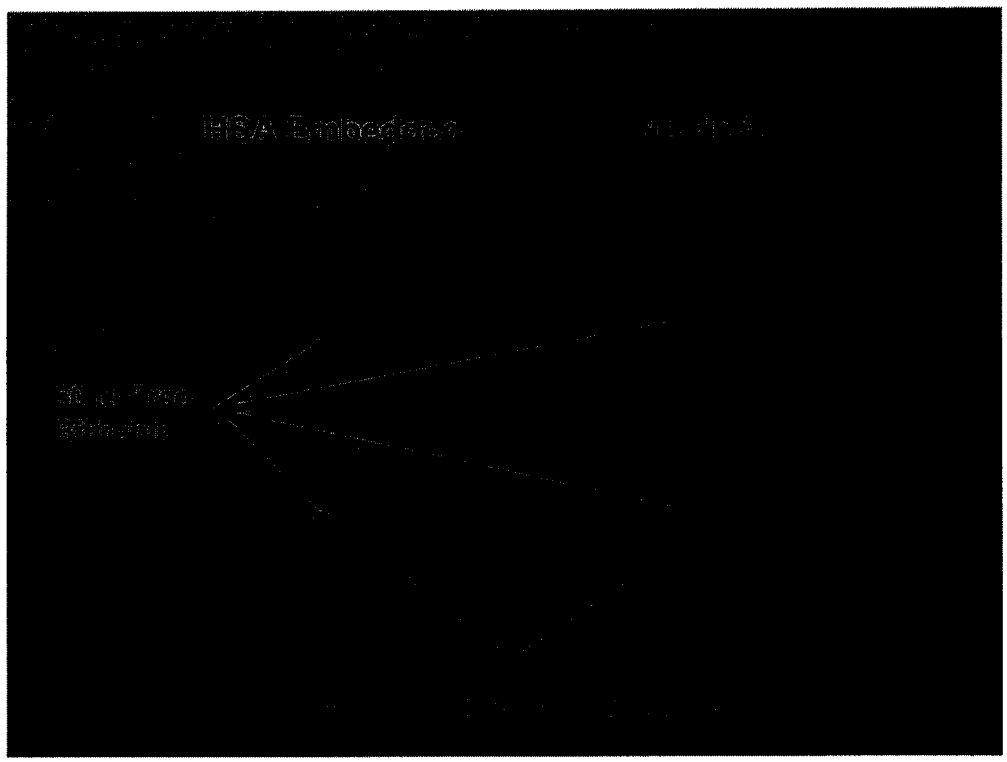
FIG. 5 shows cleaned glass slides with surface-immobilized PEG-DA (Polyethylene glycol diacrylate) polymer coated over the entire surface. Both slides have been exposed to 50 ml 0.2 mg/dl free bilirubin (Sigma) in 2 spotted areas. The left hand slide contained embedded HSA, while the right hand slide contained no HSA. Both slides were washed after the 10 minute incubation period for 2 mins with PBS buffer.

FIG. 5 shows the presence of diffused bilirubin into photocured PEG-DA (Polyethylene Diacrylate) polymer after incubation, evident by the yellow color. In this FIG. 5, 50 μl of 0.2 μg/dl laboratory free bilirubin (Sigma) in PBS buffer was incubated onto the surface of a metallized slide according to the present invention. After a 10 minute incubation period, the assay was washed with buffer for 2 mins to remove any unbound material. From the photograph shown in FIG. 5, the presence of the bilirubin can be clearly seen, confirming the plausibility of the proposed assay. In addition, this free bilirubin concentration is towards the lower end of the clinically important concentration range scale to be assayed. While no silver is present on these substrates, silver Island films only occupy a ≈40% mass surface coverage and therefore the polymer adheres to the 60% non silvered glass using the same chemistries.

Figure 8:
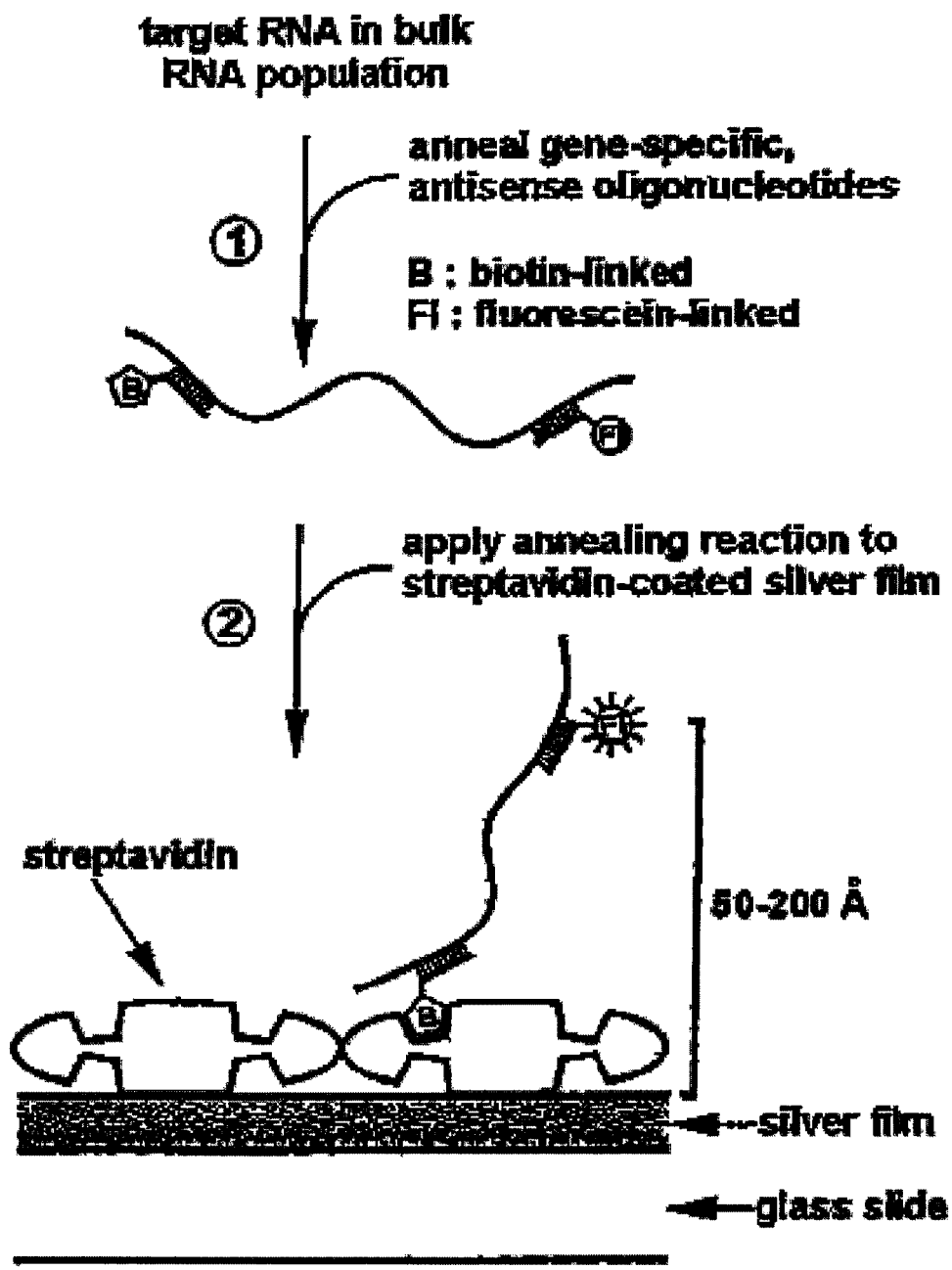
FIG. 8 shows one embodiment of the MEF-based RNA sensing platform technology of the present invention.

In an another embodiment, the present invention relates to a new sensing platform technology based on Metal-Enhanced Fluorescence (MEF), where the detected fluorescence emission is significantly amplified for detection of a nucleotide sequence. The nucleotide sequence communicatively connect to the metallic material can be quantified compared to the undetectable emission on non metallized surface. In this regard, the detection of RNA is accomplished by annealing a target RNA, tagged with a fluorophore, to an oligonucleotide anchor probe in a single step on a solid surface, where the, fluorescence signal is intrinsically enhanced by silver nanoparticles as shown in MEF based RNA sensing platform systems of FIGS. 8 and 11.

"Nucleotide," as used herein refers to deoxyribonucleic acid (DNA) or ribonucleic (RNA), RNA can be unspliced or spliced mRNA, rRNA, tRNA, or antisense RNAi. DNA can be complementary DNA (cDNA), genomic DNA, or an antisense.

The nucleotides used as hybridization probes in the present inventor are typically designed to be specific for the desired sequence in order to decrease the probability of hybridizing to unrelated sequences. Such probes can be modified so as to be detectable using radionuclides, luminescent moieties, and so forth. Hybridization conditions also can be modified in order to achieve the desired specificity. For example, a moderately stringent hybridization condition may include: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash). An example of moderately-high stringency hybridization conditions is as follows: 0.1×SSC/0.1% SDS at about 52° C. (moderately-high stringency wash). An example of high stringency hybridization conditions is as follows: 0.1×SSC/0.1% SDS at about 65° C. (high stringency wash).

The nucleotides sequences of the present invention can be obtained using standard techniques known in the art (e.g., molecular cloning, chemical synthesis) and the purity can be determined by polyacrylamide or agarose gel electrophoresis, sequencing analysis, and the like. Polynucleotides also can be isolated using hybridization or computer-based techniques that are well known in the art. Such techniques include, but are not limited to: (1) hybridization of genomic DNA or cDNA libraries with probes to detect homologous nucleotide sequences; (2) antibody screening of polypeptides expressed by DNA sequences (e.g., using an expression library); (3) polymerase chain reaction (PCR) of genomic DNA or cDNA using primers capable of annealing to a nucleic acid sequence of interest; (4) computer searches of sequence databases for related sequences; and (5) differential screening of a subtracted nucleic acid library.

Formation of Silver Island Films (SiFs) on APS-Coated Glass Substrates

Silver nitrate (99.9%), sodium hydroxide (99.996%), ammonium hydroxide (30%), trisodium citrate, D-glucose and premium quality APS-coated glass slides (75×25 mm) were obtained from Sigma-Aldrich. The sources for enzymes, RNA and DNA are described below. In a typical SiFs preparation a solution of silver nitrate (0.5 g in 60 ml of deionized water) in a clean 100-ml glass beaker, equipped with a Teflon-coated stir bar, is prepared and placed on a Corning stirring/hot plate. While stirring at the quickest speed, 200 μL of freshly prepared 5% (w/v) sodium hydroxide solution is added. This results in the formation of dark brown precipitates of silver particles. Approximately 2 ml of ammonium hydroxide is then added, drop by drop, to re-dissolve the precipitates. The clear solution is cooled to 5° C. by placing the beaker in an ice bath, followed by soaking the APS-coated glass slides in the solution. While keeping the slides at 5° C., a fresh solution of D-glucose (0.72 g in 15 ml of water) is added. Subsequently, the temperature of the mixture is then warmed to 30° C. As the color of the mixture turns from yellow-green to yellow-brown, and the color of the slides become green, the slides are removed from the mixture, washed with water, and sonicated for a few seconds at room temperature. SiFs-deposited slides were then rinsed with deionized water several times and dried under a stream of nitrogen gas.

Preparation of the β-Globin mRNA Substrate

The complete protein coding sequence of rabbit β-globin mRNA was amplified from plasmid pC7βG[23] by polymerase chain reaction using Pfu DNA polymerase (Stratagene, La Jolla, Calif.) from primers 5'-GCAG TCTAGAATGGTGCATCTGTCCAG-3' and 5'-GCAC AAGCTTCAGTGGTATTTGTGAGCCAGG-3' (Integrated DNA Technologies, Coralville, Iowa). Underlined bases indicate the XbaI and HindIII restriction sites incorporated into the 5'- and 3'-termini of the PCR product. This DNA fragment was then inserted into the XbaI+HindIII restriction sites of pGEM7Zf(+) (Promega, Madison, Wis.) using standard subcloning techniques to generate plasmid pG7(+)βG-CDS. The fidelity of the β-globin cDNA insert was verified by restriction digests and automated DNA sequencing.

Figure 12:
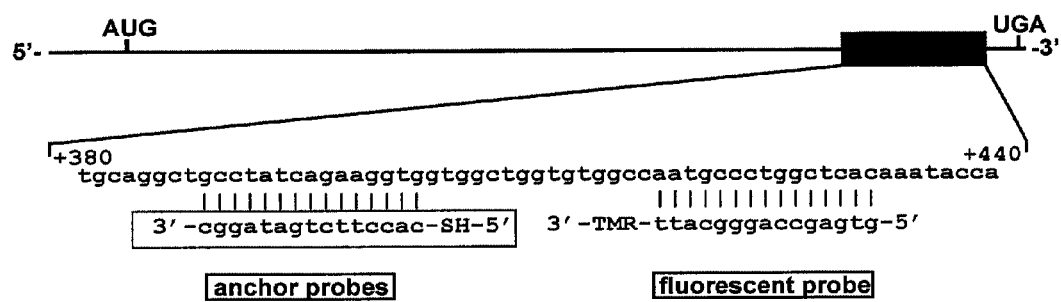
FIG. 12 shows the β-globin mRNA substrate with the positions of translational initiation (AUG) and termination (UGA) codons indicated. The 3'-coding sequences targeted by the anchor and fluorescent primers are indicated below. Base numbering is relative to the translation initiation codon Accession number for the rabbit b-globin mRNA sequence is V00879.

A 484-nt RNA substrate containing the β-globin coding sequence (See FIG. 12) was prepared by in vitro transcription using T7 RNA polymerase (Ambion, Austin, Tex.) from a HindIII-linearized pG7(+)βG-CDS DNA template. Following digestion of template DNA with RQ1-DNase (Promega), templates were purified by duplicate extractions with phenol:chloroform:isoamyl alcohol (25:24:1). Unincorporated nucleotides were removed from the preparation by spin column chromatography through RNase-free G-50 Quick Spin columns (Roche, Indianapolis, Ind.). The integrity of the β-globin RNA substrate was evaluated by electrophoresis through formaldehyde-agarose gels stained with ethidium bromide. Fluorescence intensity of ethidium bromide-stained RNA was measured using the EDAS 290 gel documentation system (Kodak, Rochester, N.Y.), with synthesis yield calculated by comparison to co-fractionated RNA size markers (InVitrogen, Carlsbad, Calif.).

MEF-Based RNA Sensing Assays

Figure 11:
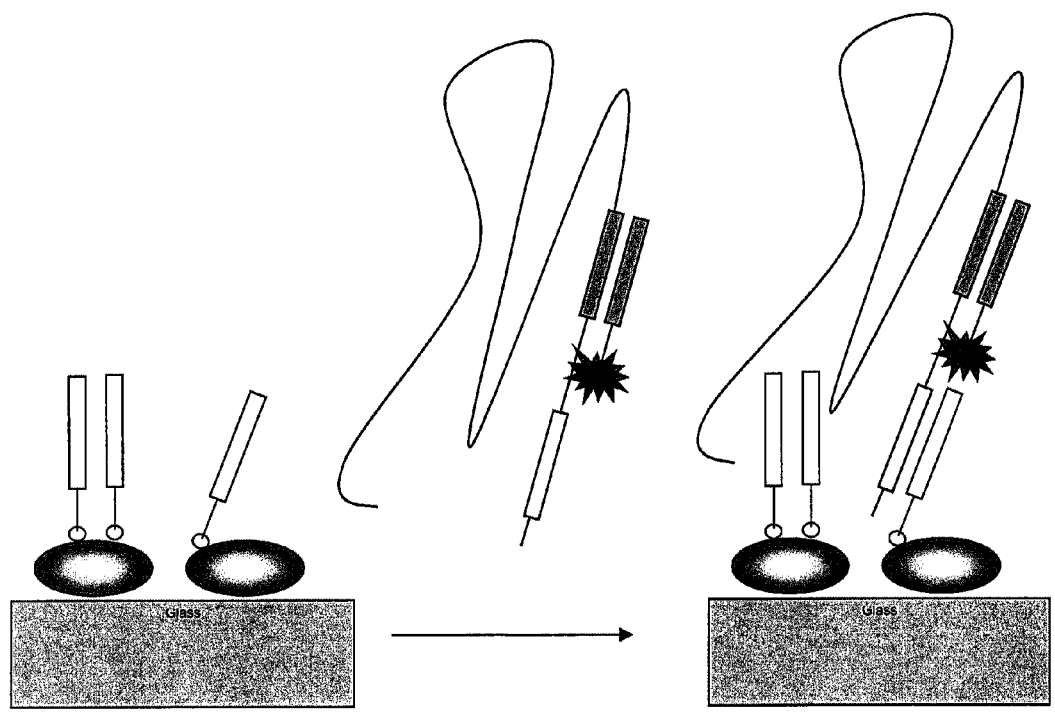
FIG. 11 shows another embodiment of the RNA biosensing assay of the present invention.
Figure 11:
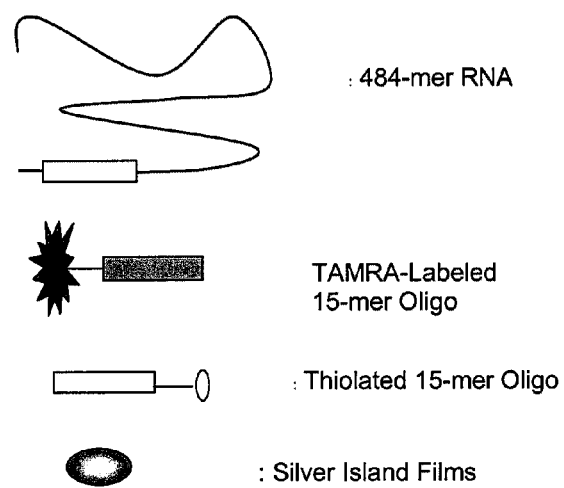

The following RNA capture assay [143] was used to detect specific RNA substrates on SiFs-coated glass slides, as shown in FIG. 11. First, β-globin mRNA or yeast tRNA substrates (10 ng) were incubated with an antisense primer 5'-GTGAGCCAGGGCATT-TAMRA-3' (fluorescent probe; 10 pmol) in a total volume of 100 μl hybridization buffer [10 mM HEPES.KOH [pH 7.4] containing 100 mM KCl, 2 mM dithiolthreitol, and 1 mM MgCl$_2$] at 70° C. for 5 minutes, then the RNA/DNA construct was slowly cooled to 37° C. over 20-30 minutes. The anchor probe (5'-thiol-CACCTTCTGATAGGC-3', 10 pmol) was attached to the SiFs by an overnight incubation at 4° C. in a humidified chamber. Excess thiol-conjugated oligo was removed by washing the surface with the hybridization buffer several times. The TAMRA-linked oligo annealed to RNA substrates were annealed to the thiol-linked anchor oligo on the surface of the SiFs at 37° C. for 30 minutes in a humidified chamber. Non-binding RNA substrates were removed as described above prior to fluorescence measurements. This procedure brings the fluorophore to a distance, approximately 10 nm, from the surface of the SiFs where the fluorescence emission is expected to increase by MEF as described previously [131, 132].

Fluorescence measurements on SiFs were performed by placing the SiFs on a stationary stage equipped with the fiber-optics mount on a 15-cm-long arm (normal to sample). The output of the fiber was connected to an Ocean Optics HD2000 spectrofluorometer for the emission spectra. The excitation light was provided by a 532 nm laser at an angle of 45 degrees. The emission spectra were observed through a 532-nm-notch filter (Samrock).

Figure 9:
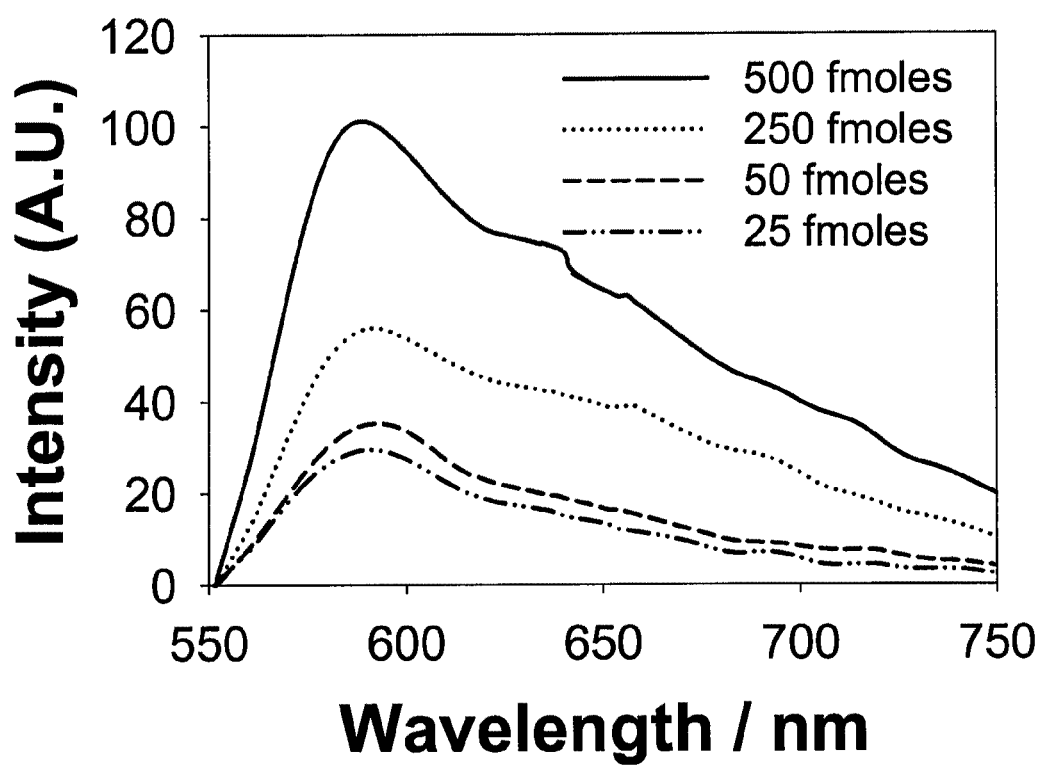
FIG. 9 shows the fluorescence emission spectra (intensity: arbitrary units) of TAMRA-linked oligo annealed to the RNA substrate that was hybridized with the thiolated Oligo anchor probe on the surface of the SiFs.
Figure 10:
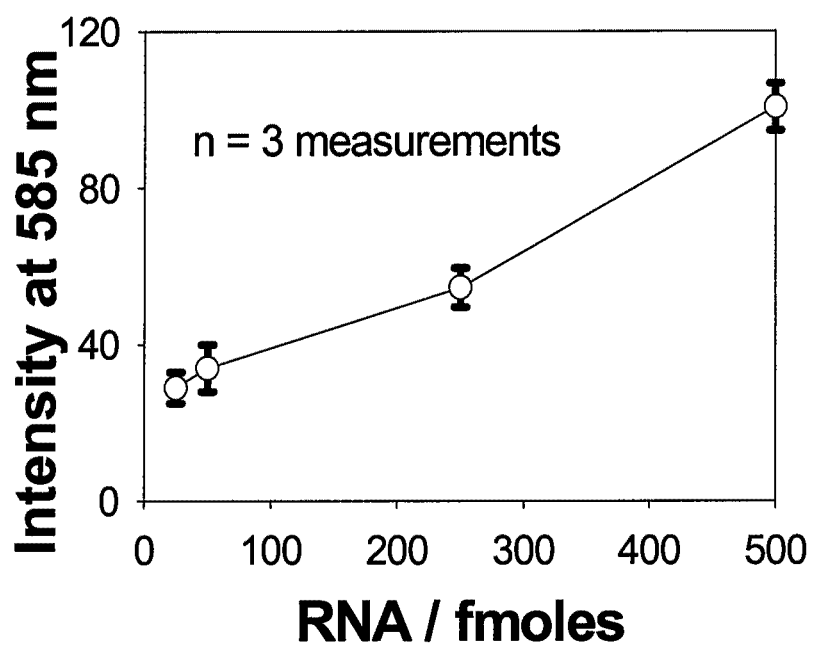
FIG. 10 shows the fluorescence emission intensity measured at 585 nm versus the amount of RNA used in the RNA capture assay (Signal to Noise, S/N>20) for three separate measurements.
Figure 13:
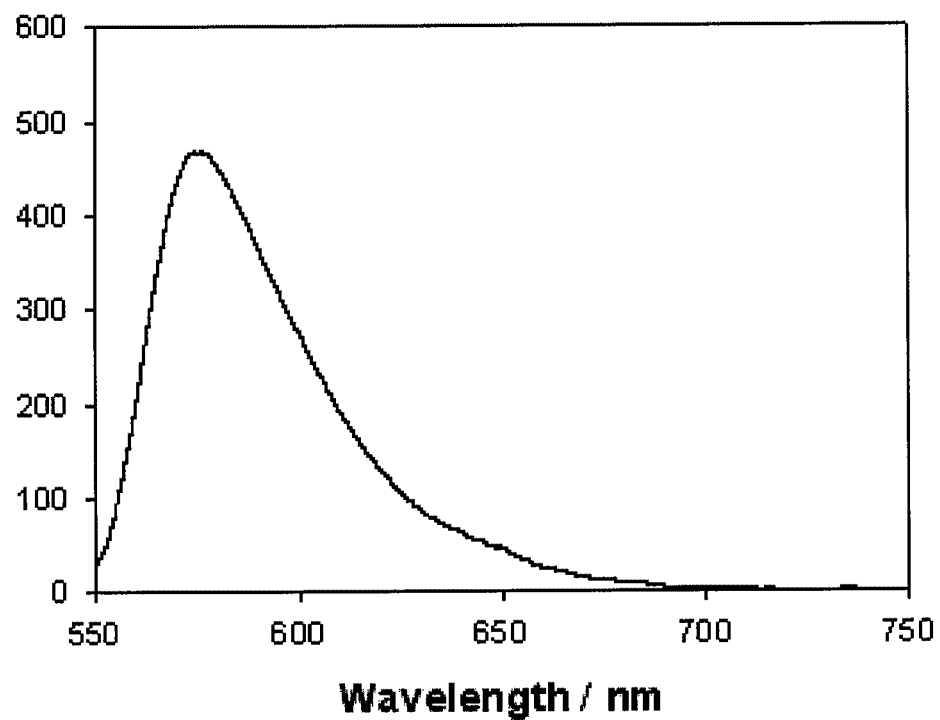
FIG. 13 shows fluorescence emission spectrum measured from a 40 uL solution of 500 fmoles of TAMRA-linked oligo anchor probe on glass slide (TAMRA-linked oligo is not linked to the surface).

The deposition of Silver Island films onto glass slides was performed as described previously [136]. In a typical SiF preparation, a solution of sodium hydroxide and ammonium hydroxide are added to a continuously stirred solution of silver nitrate at room temperature. Subsequently, the mixture is cooled down in an ice bath, Silane-prep™ glass slides (Sigma) are inserted and a solution of D-glucose is added. As the temperature is increased, the color of the mixture turns yellow-brown and the SiFs-deposited slides are removed from the mixture, washed with water, and sonicated for a few seconds at room temperature. SiFs-deposited glass slides were stored in deionized water until they were used. Fluorescence emission spectra of TAMRA-labeled oligo with RNA substrate hybridized to the thiolated-oligo anchor probe on SiFs is shown in FIG. 9. The emission intensity peak of TAMRA-labeled oligo that was annealed to RNA substrates ranging from 25 fmoles to 500 fmoles is clearly observed at 585 nm, and increased linearly as the amount of RNA substrate is increased, as shown in FIG. 9. The fluorescence emission spectra of TAMRA shown in FIG. 9 (especially for the RNA substrates of 250 fmoles or higher) appear broader than the spectrum of TAMRA-labeled oligo anchor probe measured from a solution on plain glass, as shown in FIG. 13, due to the background scattering from the SiFs-coated glass slide.

Figure 14:
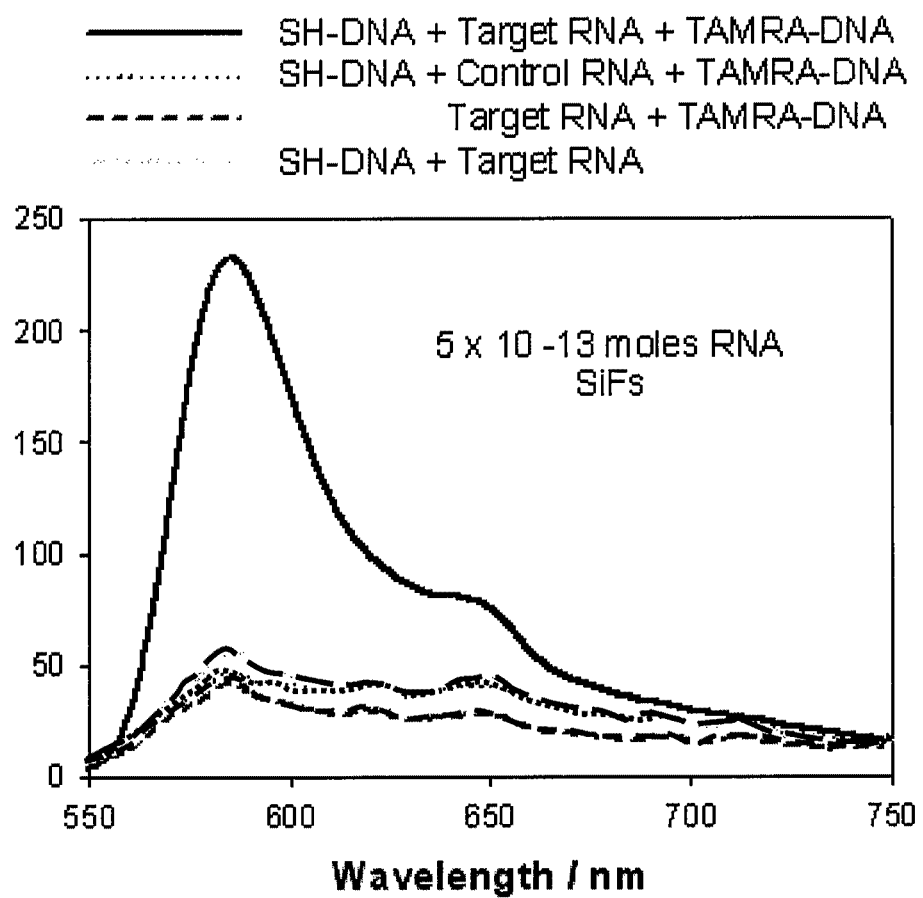
FIG. 14 shows fluorescence emission spectra (intensity: arbitrary units) of TAMRA-linked oligo annealed to the 500 fmoles of RNA substrate that was hybridized with the thiolated oligo anchor probe on the surface of the SiFs and control experiments: 1) Control RNA (tRNA, random sequence, Sigma) is used instead of Target RNA, 2) thiolated-oligo anchor probe is omitted, 3) TAMRA-linked oligo is omitted from the RNA capture assay.

The control experiments revealed that when the RNA sequence was changed (that is, control tRNA with random sequence is used in the RNA capture assay) the fluorescence emission from TAMRA-labeled oligo was not observed, as shown in FIG. 14, since the control tRNA lacked the specific sequence that is required for the annealing of TAMRA-labeled RNA. In addition, when either of the other components of the RNA capture assay, thiolated-oligo or TAMRA-labeled oligo is omitted, almost no fluorescence emission was observed. Thus, the RNA capture assay is highly specific and the contribution of the non-specific interactions to the detected signal is minimal.

The lower detection limit (LDL) of the RNA capture assay described here was 25 fmoles of RNA (S/N>20) and made possible by the amplification of fluorescence emission intensity based on our previously described phenomenon metal-enhanced fluorescence [131, 132]. The amplification of fluorescence emission intensity is a property of the silver nanoparticles deposited on the glass slides and thought to occur due to partial non-radiative energy transfer between the excited state of the fluorophore and the surface plasmons of the silver nanoparticles, as well as due to the spatially localized excitation of fluorophores created by the nanoparticles within close proximity [137].

Although the LDL of the MEF-based RNA capture assay is 100-200-fold less sensitive than the current RNA capture assays [129, 140], the MEF-based RNA sensing method offers a considerably simpler, cheaper and quicker alternative to RT-PCR, since it does not require the amplification of the RNA target and can be performed relatively quickly. Given that the S/N>3-4 for fluorescence-based assays is considered acceptable, [133] the actual lower detection limit of the MEF-based RNA capture assay is approximately 5 fmoles.

Figure 15:
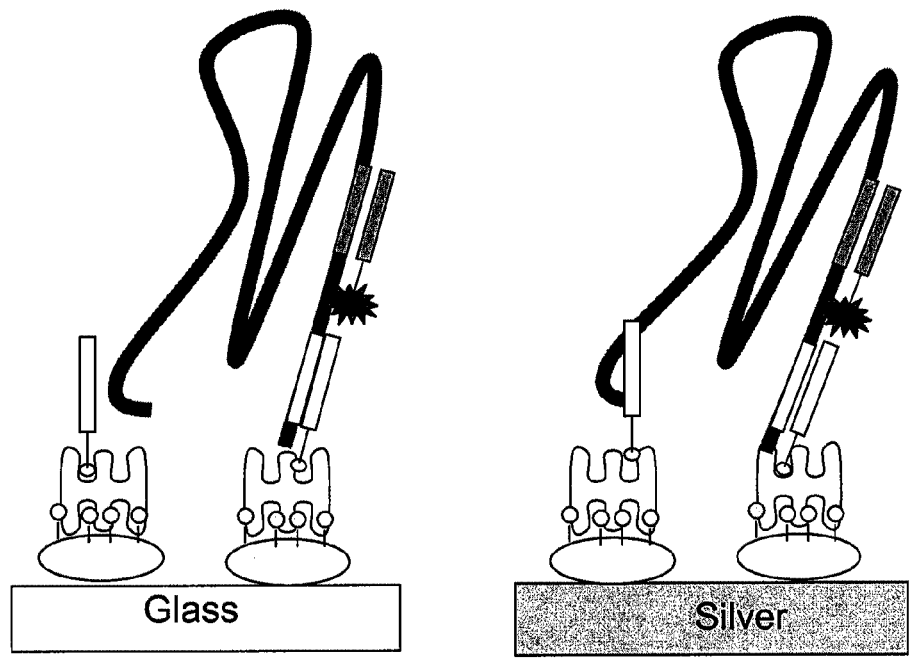
FIG. 15 shows the experimental scheme used for the detection of RNA in the absence of SiFs (on glass, Top-Left) and in the presence of SiFs using avidin-biotin interactions.
Figure 16:
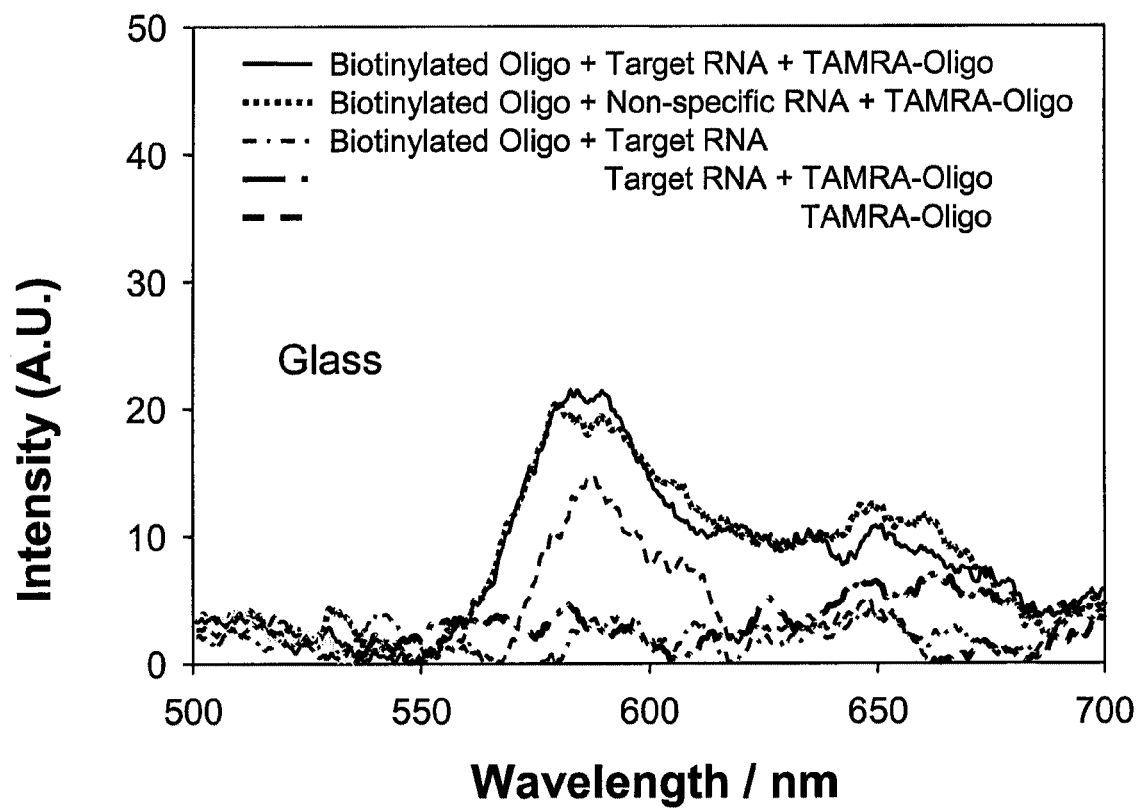
FIG. 16 shows fluorescence emission spectra (intensity: arbitrary units) of TAMRA-linked Oligo annealed to the RNA substrate (500 fmoles) that was hybridized with the biotinylated Oligo anchor probe that was brought to the glass surface via avidin-biotin interactions.
Figure 17:
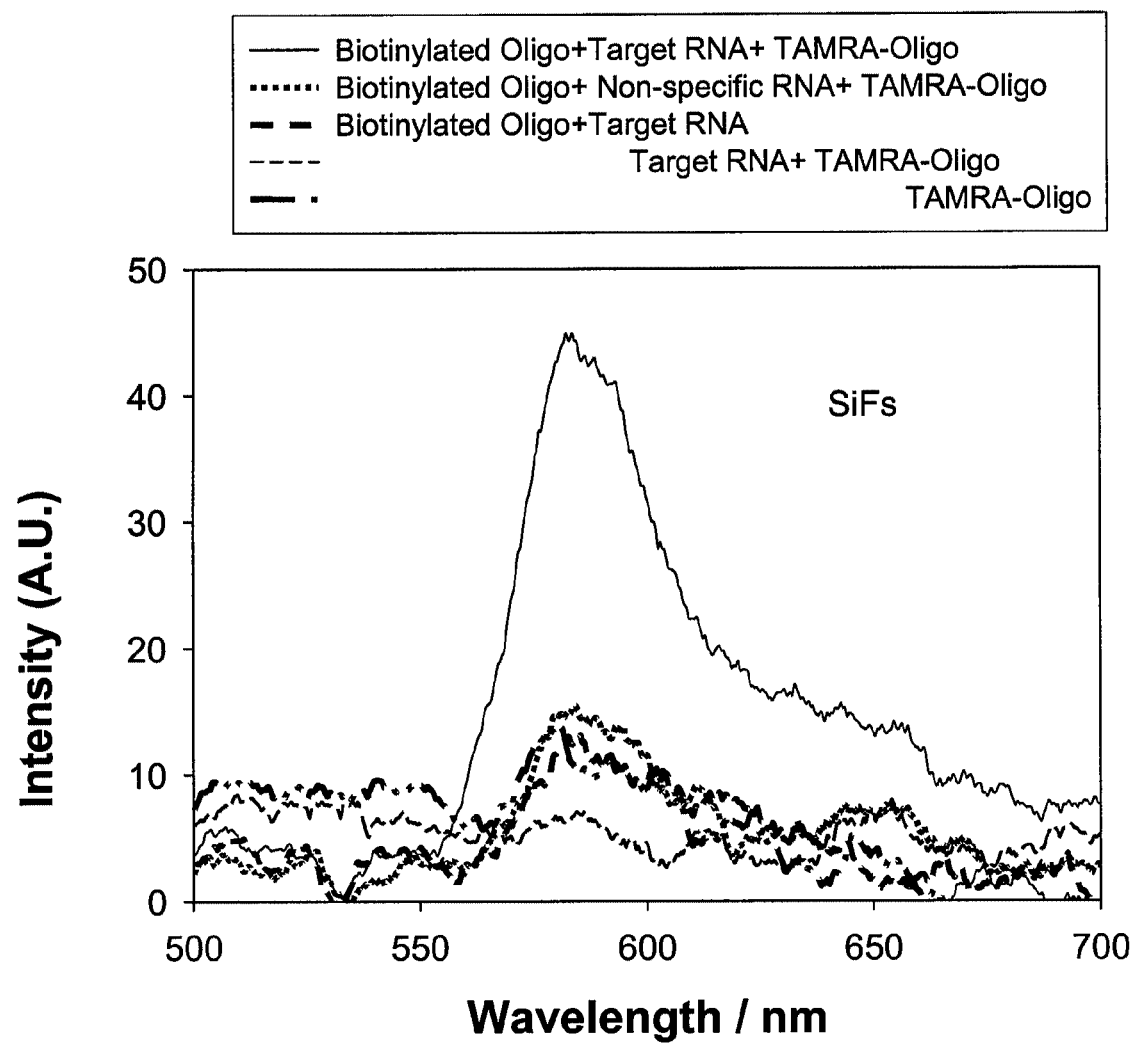
FIG. 17 shows fluorescence emission spectra (intensity: arbitrary units) of TAMRA-linked Oligo annealed to the RNA substrate (500 fmoles) that was hybridized with the biotinylated Oligo anchor probe that was brought to the SiFs-coated surface via avidin-biotin interactions.

In a comparison experiment, RNA was detected in the absence of SiFs on glass (FIG. 15 on glass, Top-Left) and in the presence of SiFs using avidin-biotin interactions. In this regard, firstly, the RNA is annealed to a TAMRA-labeled oligo and then the RNA/TAMRA-labeled oligo is annealed to a biotinylated Oligo. Finally, the resultant RNA/Oligo construct is brought the surface due to the interaction of avidin and biotin. FIG. 16 shows fluorescence emission spectra (intensity: arbitrary units) of TAMRA-linked Oligo annealed to the RNA substrate (500 fmoles) that was hybridized with the biotinylated Oligo anchor probe that was brought to the glass surface via avidin-biotin interactions. The emission intensity peak of TAMRA-labeled oligo that was annealed to RNA substrates (Target and non-specific RNA: 500 fmoles) is observed at 585 nm but are similar (20 AU). That is, the RNA assay on glass substrate in the absence of SiFs is not sensitive enough to distinguish between the actual assay and the non-specific interactions. In contrast, FIG. 17 shows fluorescence emission spectra (intensity: arbitrary units) of TAMRA-linked Oligo annealed to the RNA substrate (500 fmoles) that was hybridized with the biotinylated Oligo anchor probe that was brought to the SiFs-coated surface via avidin-biotin interactions. The emission intensity peak of TAMRA-labeled oligo that was annealed to RNA substrates (Target and non-specific RNA: 500 fmoles) is observed at 585 nm and significantly larger than the background. Although, the sensitivity of the RNA assay using SiFs (and avidin-biotin interactions) is improved compared to the assay on the glass surface, the sensitivity is much less when compared to the RNA assay on SiFs with thiolated-oligo is used. This is due to the fact that the fluorophore is located approximately 10 nm away from the surface of the silver when avidin-biotin system is used (the thicknesses of avidin and biotinylated BSA are 4 nm) and approximately 4 nm when thiolated oligo is used. In all the previously published MEF papers [131, 132, 136, 137] the maximum enhancement of fluorescence by silver was observed when the fluorophore was located within 8 nm of the surface and the enhancement is decreased for the distances larger than 8 nm. Thus, the RNA assay using the thiolated-oligo on SiFs is more sensitive than the assays using avidin-biotin interactions on glass and SiFs.

The rapidity of the MEF-based RNA capture assays could be increased further with the help of low-power microwaves, as shown previously for the MEF-based protein and antibody assays that were completed within 20 seconds, i.e., microwave-accelerated metal-enhanced fluorescence (MAMEF) [136, 138]. Similar to RT-PCR, the MEF-based RNA capture assays could potentially be multiplexed by simply using SiFs-coated high throughput screening (HTS) wells [139]. Ultimately, ultra-rapid MEF-based multiplexed RNA capture assays comparable to RT-PCR could be achieved by combining MAMEF technology with the use of SiFs-coated HTS wells once the sensitivity of the MEF-based method is improved. In this regard, MEF-based enhancements in excess 3000-fold using fractal silver surfaces was recently reported [132].

References

The contents of the following references are hereby incorporated by reference herein for all purposes:

[1] Geddes, C. D. and Lakowicz, J. R. (2002). Metal-Enhanced Fluorescence, *J. Fluorescence*, 12 (2), 121-129.

[2] Lakowicz, J. R. (2001). Radiative Decay Engineering: Biophysical and Biomedical Applications, *Anal. BioChem.*, 298, 1-24.

[3] Lakowicz, J. R., Shen, Y., D'Auria, S., Malicka, J., Fang, J., Gryczynski, Z. and Gryczynski, I. (2002). Radiative Decay Engineering 2. Effects of silver island films on fluorescence intensity Lifetimes and Resonance energy transfer, *Anal. Biochem.*, 301, 261-277.

[4] Lakowicz, J. R., Gryczynski, I, Shen, Y. B., Malicka, J., and Gryczynski, Z, (2001). Intensified fluorescence, *Photonics Spectra*, 35(10), 96-104.

[5] Gryczynski, I., Malicka, J., Gryczynski, Z., Geddes, C. D. and Lakowicz, J. R. (2002) The CFS engineers the intrinsic radiative decay rate of low quantum yield fluorophores, *J. Fluorescence*, 12(1), 11-13.

[6] Malika, J., Gryczynski, I., Maliwal, B. P., Fang, J. F. and Lakowicz, J. R. (2003). Fluorescence spectral properties of cyanine dye labeled DNA near metallic silver particles, *Biopolymers*, 72(2), 96-104.

[7] Malicka, J., Gryczynski, I., Kusba, J., Shen, Y. B., and Lakowicz, J. R. (2002). Effects of metallic silver particles on resonance energy transfer in labeled bovine serum albumin, *Biochem. Biophys. Res. Comm.*, 294(4), 886-892.

[8] Gryczynski, I., Malika, J., Shen, Y. B., Gryczynski, Z., and Lakowicz J. R. (2002). Multiphoton excitation of fluorescence near metallic particles: Enhanced and localized excitation, *J. Phys. Chem. B.*, 106(9), 2191-2195.

[9] Malika, J., Gryczynski, I., Fang, J. Y., Kusba, J. and Lakowicz, J. R. (2002). Photostability of cy3 and cy5-labeled DNA in the presence of metallic silver particles, *J. Fluorescence*, 12(3-4), 439-447.

[10] Geddes, C. D., Cao, H., Gryczynski, I., Gryczynski, Z., Fang, J. and Lakowicz, J. R. (2003). Metal-enhanced Fluorescence (MEF) Due to silver colloids on a planar surface: Potential applications of Indocyanine green to in vivo imaging, *J. Phys Chem. A.*, 107, 3443-3449.

[11] Geddes, C. D., Parfenov, A., Gryczynski, I., Malicka, J., Roll, D., and Joseph R. Lakowicz, (2003). Fractal silver structures for metal-enhanced fluorescence: Applications for ultra-bright surface assays and lab-on-a-chip based nanotechnologies, *J. Fluorescence*, 13(2), 123-128.

[12] Lakowicz, J. R., Malicka, J., Gryczynski, Z., Huang, J., Geddes, C. D. and Gryczynski, I., (2003), Increased sensitivity of Fluorescence detection, *PharmaGenomics*, 3(3), 38-46.

[13] Geddes, C. D., Parfenov, A., and Lakowicz, J. R., (2003). Photodeposition of silver can result in Metal-enhanced fluorescence, *Applied Spectroscopy*, 57(5), 526-531.

[14] Geddes, C. D., Gryczynski, I., Malicka, J., Gryczynski, Z., and Lakowicz, J. R. (2003). Metal-Enhanced Fluorescence: Potential applications in HTS, *Combinatorial Chemistry and HTS*, 6(2), 109-117.

[15] Lakowicz, J. R., Gryczynski, I., Malicka, J., Gryczynski, Z., and Geddes, C. D. (2002). Enhanced and localized multi-photon excited fluorescence near metallic silver islands: Metallic islands can increase probe photostability *J. Fluorescence*, 12(3/4), 299-302.

[16] Aslan, K., Lakowicz, J. R., and Geddes, C. D., (2005). Rapid Deposition of Triangular Silver Nanoplates on Planar Surfaces: Application to Metal-enhanced Fluorescence, *Journal of Physical Chemistry B.*, 109(13), 6247-6251,

[17] Aslan, K., Lakowicz, J. R., and Geddes, C. D., (2005). Fast and slow deposition of Silver Nanorods on Planar-Surfaces: Application to Metal-enhanced fluorescence. *Journal of Physical Chemistry B.*, 109(8), 3157-3162,

[18] Aslan, K., Lakowicz, J. R., Szmacinski, H., and Geddes, C. D., (2005). Enhanced ratiometric pH sensing using SNAFL-2 on silver island films: Metal-enhanced fluorescence sensing. *Jn. Fluorescence*, 15(1), 37-40,

[19] Wu, M., Lakowicz, J. R., and Geddes, C. D., (2005). Enhanced lanthanide luminescence using silver nanostructures: Opportunities for a new class of probes with exceptional spectral characteristics. *Jn. Fluorescence*, 15(1), 53-59, 2005.

[20] Aslan, K., Lakowicz, J. R., Szmacinski, H., and Geddes, C. D., (2004). Metal-enhanced fluorescence solution based sensing Platform. *Jn. Fluorescence*, 14 (6), 677-679, 2004.

[21] Geddes, C. D., Parfenov, A., Roll, D., Gryczynski, I., Malicka, J., and Lakowicz, J. R., (2004). Roughened silver electrodes for use in Metal-enhanced fluorescence. *Spectrochemica Acta A.*, 60 (8-9), 1977-1983,

[22] Parfenov, A., Gryczynski, I., Malicka, J., Geddes, C. D., and Lakowicz, J. R., (2003). Enhanced fluorescence from fluorophores on fractal silver surfaces. *Jn. Phys. Chem. B.*, 107(34), 8829-8833.

[23] Pugh, V. J., Szmacinski, H., Moore, W. E., Geddes, C. D., and Lakowicz, J. R., (2003). Submicrometer spatial resolution of Metal-enhanced fluorescence. *Applied Spectroscopy*, 57(12), 1592-1598,

[24] Geddes, C. D., Parfenov, A., Roll, D., Fang, J., and Lakowicz, J. R., (2003). Electrochemical and laser deposition of silver for use in metal-enhanced fluorescence. *Langmuir*, 19, 6236-6241,

[25] Lakowicz, J. R., Geddes, C. D., Malicka, J., Gryczynski, K., Lukomska, J. Huang, C., Asian, K., and Gryczynski. I., (2004). Advances in Surface-enhanced Fluorescence. *Jn. Fluorescence*, 14(4), 425-441,

[26] Aslan, K., et al and Geddes, C. D., (2005) Metal-enhanced fluorescence: An emerging tool in biotechnology. *Current opinions in Biotechnology*, 16(1), 55-62,

[27] Geddes, C. D., Aslan, K., Gryczynski. I., Malicka, J., and Lakowicz, J. R., Radiative Decay Engineering (RDE). *Topics in Fluorescence Spectroscopy Volume* 8, Edited by Chris D. Geddes and Joseph R. Lakowicz, Springer, New York, Pgs 405-448.

[28] Geddes, C. D., Aslan, K., Gryczynski. I., Malicka, J., and Lakowicz, J. R., (2004) Noble-metal surfaces for Metal-enhanced fluorescence, In *Reviews in Fluorescence* 2004, Ed by Chris D. Geddes and Joseph R. Lakowicz, Kluwer Academic Plenum Publishers, New York, pgs 365-401. ISBN: 0-306-48460-9.

[29] Aslan, K., Bagugu, R., Lakowicz, J. R., and Geddes, C. D., (2005). Metal-Enhanced Fluorescence from Plastic substrates. *Jn. Fluorescence,* 15(2), 99-104,

[30] Lakowicz, J. R., Malicka, J., Gryczynski. I., Gryczynski. Z., Geddes, C. D., (2003) Radiative Decay Engineering: The role of photonic mode density in biotechnology. *Jn. Physics D. Appl. Phys.* 38, R240-249,

[31] Volpe, J. J., (2001). Bilirubin and Brain Injury, in Neurology of the Newborn [ed 4].

[32] Amin, S. B., (2004). Clinical assessment of bilirubin-induced neurotoxicity in premature infants. *Seminars in Perinatology* 28:340-347.

[33] Amin, S. B., Charafeddine, L., Guillet, R., (2005). Transient Bilirubin Encephalopathy and Apnea of Prematurity in 28 to 32 Weeks Gestational Age Infants. *J Perinatol.* 2005.

[34] Pledger, D. R., Scott, J., Belfield, A., (1982). Kernicterus at low levels of serum bilirubin: The impact of bilirubin albumin-binding capacity. *Biol Neonate.* 1982; 41:38-44.

[35] Garziani, L. J., Mitchell, D. G., Kornhauser, M., et al., (1992). Neurodevelopment of preterm infants. Neonatal neurosonographic and serum bilirubin studies. *Pediatrics.* 89(2): 229-234.

[36] O'Shea, T. M., Dillard, R. G., Klinepeter, K. L., Goldstein, D. J., (1992). Serum bilirubin levels, intracranial hemorrhage, and the risk of developmental problems in very low birth weight neonates. *Pediatrics.* 90(6):888-892.

[37] Van de Bor, M., Dokkum, M. E., Schreuder, A. M., Veen, S., Brand, R., Verloove-Vanhorick, S. P., (1992). Hyperbilirubinemia in low birth weight infants and outcome at 5 years of age. *Pediatrics.* 89(3):359-364.

[38] Hansen, T. W., (1996). Therapeutic approaches to neonatal jaundice: an international survey. *Clin Pediatr.* 35(6):309-316

[39] Bratlid, D. (1990). How bilirubin gets into the brain. *Clin Perinatol.* 17:449-465.

[40] Ahlfors, C. E. (2001). Bilirubin-albumin binding and free bilirubin. *J. Perinatol.* 21: S40-42

[41] Amin, S. B., Ahlfors, C., Orlando, M. S., Dalzell, L. E., Merle, K. S., Guillet, R., (2001). Bilirubin-albumin binding variables in premature infants. *Pediatrics* 107(4):664-668.

[42] Nakamura, H., Yonetani, M., Uetani, Y., Funato, M., Lee, Y., (1992). Determination of serum unbound bilirubin for prediction of kernicterus in low birth weight infants. *Acta. Paediatr. Jpn.* 34:642-647.

[43] Cashore, W. J., Oh, W., (1982). Unbound bilirubin and kernicterus in low birth weight infants. *Pediatrics* 69(4):481-485.

[44] Ritter, D. A., Kenney, J. D., Norton, H. J., Rudolph, A. J., (1982). A prospective study of free bilirubin and other risk factors in the development of kernicterus in premature infants. *Pediatrics* 69(3):260-266.

[45] Nakamura, H., Takada, S. Shimabuku, R., et al. (1985). Auditory nerve and brainstem responses in newborn infants with hyperbilirubinemia. *Pediatrics.* 75:703-708.

[46] Funato, M., Tamai, H., Shimada, S., et al. (1994) Vigintiphobia, unbound bilirubin, and auditory brainstem responses. *Pediatrics.* 93:50-53.

[47] Jacobsen, J. and Wennburg, P., (1974). Determination of Unbound Bilirubin in the Serum of Newborns. *Clin. Chem.* 20(7): 783-789.

[48] Ahlfors, C., (1981). Effect of Serum Dilution on Apparent Unbound Bilirubin Concentration as Measured by the Peroxidase Method. *Clin. Chem.* 27(5): 692-696.

[49] Ahlfors, C., (2000). Measurement of Plasma Unbound Unconjugated Bilirubin. *Anal. Biochem.* 279: 130-135.

[50] Porter, E, and Waters, W., (1966). A rapid micromethod for measuring the reserve albumin binding capacity in serum from newborn infants with hyperbilirubinemia. *J. Lab & Clin. Med.* 67(4):660-668.

[51] Berde, C., Benitz, W., Rasmussen F., et al., Bilirubin Binding in the Plasma of Newborns: Critical Evalutation of a Fluorescence Quenching Method and Comparison to the Peroxidase Method., (1984) *Pediatric Research.* 18(4): 349-354.

[52] Blackmon, L. R., Fanaroff A. A., and Raju, T. N. K., (2004). Research on prevention of bilirubin-induced brain injury and kernicterus: National Institute of Child Health and Human Development Conference Executive Summary. *Pediatrics* 114:229-233.

[53] Flelschmann, M., Hendra, P. J., and McQuillan, A. J. (1974). Raman spectra of pyridine absorbed at a silver electrode, *Chem. Phys. Lett.,* 26(2), 163-166.

[54] Jeanmaire, D. L. and Van Duyne, R. P. (1997). Surface Raman spectroelectrochemistry. Part 1. Heterocyclic, aromatic and aliphatic amines adsorbed on the anodised silver electrode, *J. Electroanal. Chem.,* 84, 1-20.

[55] Aroca, R., Jennings, C., Kovacs, G. J., Loutfy, R. G. and Vincett, P. S. (1985). Surface-enhanced Raman scattering of Langmuir-Blodgett monolayers of phthalocyanine by indium and silver island films, *J. Phys. Chem.,* 89, 4051-4054.

[56] Pettinger, B., and Gerolymatou, A. (1984). Dyes adsorbed at Ag-colloids: Substitution of fluorescence by similarly efficient surface fluorescence and surface Raman scattering, *Ber. Bungens. Phys. Chem.,* 88, 359-363.

[57] DeSaja-Gonzalez, J., Aroca, R., Nago, Y. and DeSaja, J. A. (1997). Surface enhanced fluorescence and SERS spectra of N-octadecyl-3, 4:9, 10-perylenetetracarboxylic monohydride on silver island films, *Spectrochim. Acta*. Part A, 53, 173-181.

[58] Hildebrandt, P. and Stockburger, M., (1984). *J. Phys Chem. B.,* 88, 5935.

[59] Kneipp, K., Wang, Y., Kneipp, H., Itzkan, L., Dasari, R. R. and Feld, M. S., (1996). *Phys. Rev. Lett.,* 76, 2444.

[60] Kneipp, K., Wang, Y., Kneipp, H., Perelman, L. T., Itzkan, L., Dasari, R. R., and Feld, M. S., (1997). *Phys. Rev. Lett.,* 78, 1667.

[61] Axelrod, D., Hellen, E. H. and Fulbright, R. M. (1992). Total internal reflection fluorescence, in *Topics in Fluorescence Spectroscopy*, Vol. 3: *Biochemical applications*, (Lakowicz J. R., Ed.), Plenum Press, New York, pp. 289-343.

[62] Wokaun, A., Lutz, H.-P., King, A. P., Wild, U. P. and Ernst, R. R. (1983). Energy transfer in surface enhanced fluorescence, *J. Chem. Phys.,* 79(1), 509-514.

[63] Holland, W. R. and Hall, D. G. (1985). Waveguide mode enhancement of molecular fluorescence. *Optics Letts.,* 10(8), 414-416.

[64] Glass, A. M., Liao, P. F., Bergman, J. G. and Olson, D. H. (1980). Interaction of metal particles with adsorbed dye molecules: absorption and luminescence. *Optics Letts.,* 5(9), 368-370.

[65] Axelrod, D., Burghardt, T. P. and Thompson, N. L. (1984). Total internal reflection fluorescence, *Ann. Rev. Biophys. Bioeng.*, 13, 247-268.

[66] Benner, R. E., Dornhaus, R. and Chang, R. K. (1979). Angular emission profiles of dye molecules excited by surface lasmon waves at a metal surface, *Optics Commun.*, 30(2), 145-149.

[67] Barnes, W. L. (1998). Fluorescence near interfaces: The role of photonic mode density, *J. Modern Optics*, 45(4), 661-699.

[68] Camplon, A., Gallo, A. R., Harris, C. B., Robota, H. J. and Whitmore, P. M. (1980). Electronic energy transfer to metal surfaces: A test of classical image dipole theory at short distances, *Chem. Phys. Letts.*, 73(3), 447-450.

[69] Sokolov, K., Chumanov, G. and Cotton, T. M. (1998). Enhancement of molecular fluorescence near the surface of colloidal metal films, *Anal. Chem.*, 70, 3898-3905.

[70] Hayakawa, T., Selvan, S. T. and Nogami, M. (1999). Field enhancement effect of small Ag particles on the fluorescence from $Eu^{3+}$-doped $SiO_2$ glass, *Appl. Phys. Lett.*, 74(11), 1513-1515.

[71] Geddes, C. D., Cao, H., and Lakowicz, J. R. (2003). Enhanced photostability of ICG in close proximity to Gold colloids, *Spectrochemica Acta A.* 59, 2611-2617.

[72] Selvan, S. T., Hayakawa, T. and Nogami, M. (1999). Remarkable influence of silver islands on the enhancement of fluorescence from $Eu^{3+}$ ion-doped silica gels, *J. Phys. Chem. B.*, 103, 7064-7067.

[73] Strickler, S. J. and Berg, R. A. (1962). Relationship between adsorption intensity and fluorescence lifetime of molecules, *J. Chem. Phys.*, 37, 814-822.

[74] Knudsen, A., Pedersen, A. O., Brodersen, R., (1986). Spectroscopic Properties of Bilirubin-Human Serum Albumin Complexes: A Stoichiometric Analysis. *Arch. Biochem and Biophys.* 244(1): 273-284.

[75] Rivas, L., Sanchez-Cortes, S., Garcia-Ramos, J. V. and Morcillo, G. (2001), Growth of silver colloidal particles obtained by citrate reduction to increase the Ramen enhancement factor, *Langmuir*, 17(3), 574-577.

[76] Shirtcliffe, N., Nickel, U. and Schneider, S. (1999). Reproducible preparation of silver sols with small particle size using borohydride reduction: For use as nuclei for preparation of larger particles, *J. Colloid Interface Sci.*, 211(1), 122-129.

[77] Pastoriza-Santos, I., and Liz-Marzan, L. M. (2000). Reduction of silver nanoparticles in DMF. Formation of monolayers and stable colloids, *Pure Appl. Chem.*, 72(1-2), 83-90.

[78] Pastoriza-Santos, I., Serra-Rodriguez, C. and Liz-Marzan, L. M. (2000). Self-assembly of silver particle monolayers on glass from $Ag^+$ solutions in DMF, *J. Colloid Interface Sci.*, 221(2), 236-241.

[79] Bright, R. M., Musick, M. D. and Natan, M. J. (1998). Preparation and characterization of Ag colloid monolayers, *Langmuir*, 14(20), 5695-5701.

[80] Ni, F. and Cotton, T. M. (1986). Chemical procedure for preparing surface-enhanced Raman scattering active silver films, *Anal. Chem.*, 58(14), 3159-3163.

[81] Freeman, R. G., Grabar, K. C., Allison, K. J., Bright, R. M., Davis, J. A., Guthrie, A. P., Hommer, M. B., Jackson, M. A., Smith, P. C., Walter, D. G. and Natan, M. J. (1995). Self-assembled metal colloid monolayers: An approach to SERS substrates, *Science*, 267, 1629-1632.

[82] Grabar, K. C., Freeman, R. G., Hommer, M. B. and Natan, M. J. (1995). Preparation and characterisation of Au colloid monolayers, *Anal. Chem.*, 67, 735-743.

[83] Link, S, and El-Sayed, M. A. (1999). Spectral properties and relaxation dynamics of surface plasmon electronic oscillations in gold and silver nanodots and nanorods, *J. Phys. Chem. B.*, 103, 8410-8426.

[84] Kreibig, U. and Genzel, L. (1985). Optical absorption of small metallic particles, *Surface Science*, 156, 678-700.

[85] Krelbig, U., Gartz, M. and Hilger, A. (1997). Mie resonances: Sensors for physical and chemical cluster interface properties, *Ber. Bunsenges, Phys. Chem.*, 101(11), 1593-1604.

[86] Toshima, N. and Yonezawa, T. (1998). Bimetallic nanoparticles-novel materials for chemical and physical applications, *New J. Chem.*, 1179-1201.

[87] Caruso, F., Caruso, R. A. and Mohwald, H. (1998). Nanoengineering of inorganic and hybrid hollow spheres by colloidal templating, *Science*, 282, 1111-1114.

[88] Yee, J. K., Parry, D. B., Caldwell, K. D. and Harris, J. M. (1991). Modification of quartz surfaces via thiol-disulphide interchange, *Langmuir*, 7, 307-313.

[89] Farmer, S. C. and Patten, T. E. (2000). Synthesis of luminescent organic/inorganic polymer nanocomposites, *Polym. Mater. Sci. Eng.*, 82, 237-238.

[90] Comor, M. I. And Nedeljkovic, J. M. (1999). Enhanced photocorrosion stability of colloidal cadmium sulphide-silica nanocomposites, *J. Mater. Sci. Lett.*, 18, 1583-1585.

[91] Gryczynski, I., Malicka, J., Nowaczyk, K., Gryczynski, Z., and Lakowicz, J. R. (2004). Effects of Sample thickness on the Optical Properties of Surface Plasmon-Coupled Emission. *J. Phys Chem. B.*, 108, 12073-12083.

[92] Gryczynski, I., Malicka, J., Gryczynski, Z., Nowaczyk, K., and Lakowicz, J. R. (2004). Ultraviolet Surface Plasmon-Coupled Emission Using Thin Aluminum Films. *Anal. Chem.*, 76(21), 4076-4081.

[93] Geddes, C. D., Douglas, P., Moore, C. P., Wear, T. J., Egerton, P. L., (1999) Optical thin film sensors for the determination of aqueous halide Ions. *Jn. Fluorescence*, 9(3), 163-171, 1999.

[94] Geddes, C. D., and Douglas, P., (2005). Fluorescent dyes bound to hydrophilic copolymers—Applications for aqueous halide sensing. *App. Poly. Sci.*, 76(5), 603-615, 2000.

[95] Geddes, C. D., Optical thin film polymeric sensors for the determination of aqueous chloride, bromide and iodide ions at high pH, based on the quenching of fluorescence of two acridinium dyes. *Dyes and Pigments*, 45(3), 243-251, 2000.

[96] Geddes, C. D., A Halide sensor based on the quenching of fluorescence of an immobilised indolium salt. *Photochemistry and Photobiology A: Chemistry*, 137(2-3), 145-153, 2000.

[97] Geddes, C. D., Halide sensing using the SPQ molecule. *Sensors and Actuators Chemical*, 72(2), 188-195, 2001.

[98] Mills, A., and Chang, Q., (1994). Colorimetric polymer film sensors for dissolved carbon dioxide. *Sensors and Actuators B: Chemical*, 21, 83-89.

[99] Herrero, M., Tiemblo, P., Reyes-Labarta, J., Mijangos, C., and Reinecke, H., (2002). PVC modification with new functional groups. Influence of hydrogen bonds on reactivity, stiffness and specific volume. *Polymer*, 43, 2631-2636.

[100] Yu, Z. J., Kang, E. T., Neoh, K. G., and Tan, K. L., (2001). Surface Passivation of epoxy resin with a covalently adhered poly(tetrafluoroethylene) layer. *Surface & Coatings Technology*, 138, 48-55.

[101] Endo, K., (2002) Synthesis and Structure of poly (vinyl chloride). *Progess in Polymer Science*, 27, 2021-2054.

[102] James, N. R., and Jayakrishnan, A., (2003). Surface thiocyanation of plasticized poly(vinyl chloride) and its effect on bacterial adhesion. *Biomaterials*, 24, 2205-2212.

[103] Liu, B., Yang, Y., Zhao-Yang, W., Wang, H., Shen, G., and Yu, R., (2005) A potentiometric acetylcholinesterase biosensor based on plasma-polymerized film. *Sensors and Actuators B: Chemical*, 104, 186-190.

[104] Geddes, C. D., Parfenov, A., and Lakowicz, J. R. (2003). Luminescent Blinking from Noble-metal Nanostructures: New Probes for localization and imaging. *Jn. Fluorescence*, 13(4), 297-299,

[105] Geddes, C. D., Parfenov, A., Gryczynski, I., and Lakowicz, J. R. (2003). Luminescent blinking from silver nanostructures. *Jn. Phys. Chem. B.* 107(37), 9989-9993,

[106] Geddes, C. D., Parfenov, A., Gryczynski, I., and Lakowicz, J. R., (2003). Luminescent blinking of gold nanoparticles. *Chem. Phys. Letts,* 380(3-4), 269-272, 2003.

[107] Lakowicz, J. R. (1999). Principles of Fluorescence Spectroscopy, $2^{nd}$ Edition, Kluwer Academic Plenum Publishers, New York.

[108] Turro, N. J., (1991). Modern Molecular Photochemistry, University Science Books, California. ISBN 0-935702-71-7

[109] Wayne, C. E., and Wayne, R. P. (1999) Photochemistry, Oxford University Primers, Bath, ISBN 0-19-855886-4

[110] DeGraff, A., and Demas, J. N., (2005) Luminescence-Based Oxygen Sensors. Reviews In Fluorescence 2005. Springer, New York, 125-151.

[111] Lamola, A., Eisinger, J., Blumberg, W., Patel S., Flores J., (1979). Fluorometric Study of the Partition of Bilirubin among Blood Components: Basis for Rapid Microassays of Bilirubin Binding Capacity in Whole Blood. *Anal. Biochem.* 100:25-42.

[112] Geddes, C. D., (2001). Optical halide sensing using fluorescence quenching: Theory, simulations and applications—A review. An invited review article commissioned by the *Institute of Physics. Meas. Sci. Technol.,* 12(9), R53-R88.

[113] Matveeva, E., Gryczynski, Z., Malicka, J., Gryczynski, I., and Lakowicz, J. R. (2004). Metal-enhances fluorescence immunoassays using total internal reflection and silver island-coated surfaces. *Anal. BioChem.,* 334, 303-311.

[114] Malicka, J., Gryczynski, I., Gryczynski, Z., and Lakowicz, J. R. (2004). Use of Surface Plasmon-Coupled Emission to measure DNA Hybridization. *Journal of Biomolecular screening.* 9(3), 208-214.

[115] Matveeva, E., Gryczynski, Z., Gryczynski, I., Malicka, J., and Lakowicz, J. R. (2004). Myoglobin Immunoassay Utilizing Directional Surface Plasmon-Coupled Emission. *Anal. Chem.,* 76(21), 6287-6292.

[116] Matveeva, E., Malicka, J., Gryczynski, I., Gryczynski, Z., and Lakowicz, J. R. (2004). Multi-wavelength immunoassays using surface plasmon coupled emission. *Biochemical and Biophysical Research Communications.,* 313, 721-726.

[117] Ludbrook, J., (2002). Statistical Techniques for Comparing Measurers and Methods of Measurement: A Critical Review. *Clin. and Expt Pharm. and Physiol.* 29: 527-536.

[118] Ludbrook, J., (1997). Comparing methods of measurement. *Clin. and Expt Pharm. and Physiol.* 24: 193-203.

[119] Krumlauf, R. *Mol. Biotechnol.,* 1994, 2, 227-242.

[120] Elkahloun, A. G.; Gaudet, J.; Robinson, G. S.; Sgroi. D. C. *Cancer Biol. Ther.* 2002, 1, 354-358.

[121] Wilson, G. M.; Deeley, R. G. *Plasmid* 1995, 33, 198-207.

[122] Kindler, S.; Wang, H.; Richter, D.; Tiedge, H. *Annu. Rev. Cell. Dev. Biol.* 2005, 21, 223-45.

[123] van Doorn, L. J.; Kleter, B.; Voermans, J.; Maertens, G.; Brouwer, H.; Heijtink, R.; Quint, W., *J. Med. Virol.* 1994. 42, 22-28.

[124] Call, D. R.; Borucki, M. K.; Loge, F. J. *J. Microbiol. Methods* 2003, 53, 235-243.

[125] Ramaswamy, S.; Golub, T. R. *J. Clin. Oncol.,* 2003, 20, 1932-1941.

[126] Haines, D. S.; Gillespie, D. H. *Biotechniques* 1992, 12, 736-741.

[127] Rosenau, C.; Kaboord, B.; Qoronfleh. M. W. *Biotechniques* 2002, 33, 1354-1358.

[128] Bustin, S. A. *J. Mol. Endocrinol.* 2002, 29, 23-39.

[129] Tsai, S. P.; Wong, A.; Mai, E.; Chan, P.; Mausisa, G.; Vasser, M.; Jhurani, P.; Jakobsen, M. H.; Wong, W. L. T.; Stephan. J.-P. *Nucleic Acids Res.,* 2003, 31, e25.

[130] The sensitivity of RNA detection becomes limiting when only minute quantities of biological material are available (e.g. few bacterial cells or spores from an air or soil sample). This is also reflected in poor signal-to-noise when the RNA of interest is expressed at very low levels relative to the bulk RNA population (e.g. expression of oncogene mRNAs as a function of total cell RNA mass, low levels of viral mRNAs in a blood sample from a patient with a latent infection). The Rapidity is highly desirable in an RNA sensing system, particularly in microbial screening, since early identification of pathogens provides better opportunities for containment, decontamination, and treatment.

[131] Aslan, K.; Gryczynski I.; Malicka J.; Matveeva E.; Lakowicz, J. R.; Geddes, C. D. *Current Opinion in Biotechnology,* 2005, 16(1), 55-62.

[132] Parfenov, A.; Gryczynski, I.; Malicka, J.; Geddes, C. D.; Lakowicz, J. R.; *J. Phys. Chem. B.,* 2003, 107, 8829-8833.

[133] Lakowicz, J. R. *Principles of Fluorescence Spectroscopy,* 1999, Kluwer, New York.

[134] Malicka, J.; Gryczynski, I.; Gryczynski, Z.; Lakowicz J. R. *J. Biomol Screen.* 2004, 9(3), 208-215.

[135] Sastry, M.; Mayya, K. S.; Bandyopadhyay, K. *Coll. Surf. A,* 1997, 127 (1-3), 221-228.

[136] Aslan, K.; Geddes, C D. *Anal. Chem.,* 2005, 77(24), 8057-8067.

[137] Aslan, K.; Leonenko, Z.; Lakowicz, J. R.; Geddes, C. D. *J. Fluores.* 2005, 15(5), 643-654.

[138] Aslan, K.; Geddes, C. D. J. Fluores. DOI:10.1007/s10895-005-0026-z

[139] Aslan, K.; Holley, P.; Geddes, C. D. *J. Immun. Methods* (Submitted).

[140] Xie, H.; Yu, Y. H.; Xie, F.; Lao, Y. Z.; Gao, Z. *Anal. Chem.* 2004, 76, 4023-4029.

[141] Wilson, G. M., and Deeley, R. G. (1995) An episomal expression vector system for monitoring sequence-specific effects on mRNA stability in human cell lines. *Plasmid* 33:198-207.

[142] Sambrook, J., Fritsch, E. F., and Maniatis, T (1989) *Molecular Cloning: A Laboratory Manual,* $2^{nd}$ ed. Cold Spring Harbor: Cold Spring Harbor Laboratory, NY.

[143] Tsai, S. P., Wong, A., Mai, E., Chan, P., Mausisa, G., Vasser, M., Jhurani, P., Jakobsen, M. H., Wong, W. L. T., and Stephan, J.-P. (2003) Nucleic acid capture assay, a new method for direct quantitation of nucleic acids. *Nucleic Acids Res.* 31:e25.

That which is claimed:

1. A method for capturing a target RNA or DNA in a sample, the method comprising:
   a) providing a metallized surface at least partially coating a substrate, wherein the metallized surface further comprises an anchor probe, wherein the metallized surface comprises metallic islands, nanostructures, or colloids;
   b) preparing a first nucleotide sequence probe-essentially complementary to the target RNA or DNA for binding to one area of the target RNA or DNA, wherein the first nucleotide sequence probe is directly attached to a fluorescence label;
   c) preparing a second nucleotide sequence probe essentially complementary to the target RNA, or DNA wherein the second nucleotide probe binds to a region of the target RNA or DNA sequence different from and at a predetermined distance from the binding of the first probe and wherein the second nucleotide sequence probe is directly attached to a linking molecule having binding affinity for the anchor probe;
   d) providing annealing conditions for binding the first and second nucleotide sequence probes to any target RNA or DNA in the sample; and
   e) providing annealing conditions for binding the linking molecule to the anchor probe, wherein the linking molecule is positioned a sufficient distance from the fluorescence label to position the fluorescence label a distance of about 50 Å to about 200 Å from the metallized surface for enhanced fluorescence upon single or multiple photon excitation.

2. The method according to claim 1, wherein the excitation energy is generated by an electromagnetic energy source that generates single or multiple photons.

3. The method according to claim 2, wherein the electromagnetic energy source is a laser diode, light emitting diode source or a pulsing system thereof.

4. The method according to claim 1, wherein the metallized surface is fabricated of at least a noble metal.

5. The method according to claim 4, wherein the noble metal is silver, gold, platinum, copper or a combination thereof.

6. The method according to claim 2, wherein the substrate comprises glass, polymeric or combinations thereof.

7. The method according to claim 1, wherein the linking probe and anchor probe are nucleotide sequences.

* * * * *

SEQUENCE LISTING

<160> NUMBER OF SEQ ID NOS: 7

<210> SEQ ID NO 1
<211> LENGTH: 27
<212> TYPE: DNA
<213> ORGANISM: Artificial Sequence
<220> FEATURE:
<223> OTHER INFORMATION: Synthetic Construct

<400> SEQUENCE: 1
gcagtctaga atggtgcatc tgtccag                                27

<210> SEQ ID NO 2
<211> LENGTH: 31
<212> TYPE: DNA
<213> ORGANISM: Artificial Sequence
<220> FEATURE:
<223> OTHER INFORMATION: Synthetic construct

<400> SEQUENCE: 2
gcacaagctt cagtggtatt tgtgagccag g                           31

<210> SEQ ID NO 3
<211> LENGTH: 15
<212> TYPE: DNA
<213> ORGANISM: Artificial Sequence
<220> FEATURE:
<223> OTHER INFORMATION: Synthetic construct

<400> SEQUENCE: 3
gtgagccagg gcatt                                             15

<210> SEQ ID NO 4
<211> LENGTH: 15
<212> TYPE: DNA
<213> ORGANISM: Artificial Sequence
<220> FEATURE:
<223> OTHER INFORMATION: Synthetic Construct

<400> SEQUENCE: 4
caccttctga taggc                                             15

<210> SEQ ID NO 5
<211> LENGTH: 15
<212> TYPE: DNA
<213> ORGANISM: Artificial Sequence
<220> FEATURE:
<223> OTHER INFORMATION: Synthetic Construct

<400> SEQUENCE: 5
cggatagtct tccac                                             15

<210> SEQ ID NO 6
<211> LENGTH: 15
<212> TYPE: DNA
<213> ORGANISM: Artificial Sequence
<220> FEATURE:
<223> OTHER INFORMATION: Synthetic Construct

<400> SEQUENCE: 6
ttacgggacc gagtg                                             15

<210> SEQ ID NO 7
<211> LENGTH: 61
<212> TYPE: DNA

```
<213> ORGANISM: Artificial Sequence
<220> FEATURE:
<223> OTHER INFORMATION: Synthetic Construct

<400> SEQUENCE: 7
tgcaggctgc ctatcagaag gtggtggctg gtgtggccaa tgccctggct cacaaatacc    60
a                                                                   61
```